(12) United States Patent
Senger et al.

(10) Patent No.: US 6,596,276 B1
(45) Date of Patent: Jul. 22, 2003

(54) METHOD FOR INHIBITING TUMOR ANGIOGENESIS IN A LIVING SUBJECT

(75) Inventors: Donald R. Senger, Medfield, MA (US); Michael Detmar, Arlington, MA (US); Kevin P. Claffey, Burlington, CT (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/532,310

(22) Filed: Mar. 22, 2000

Related U.S. Application Data

(63) Continuation of application No. PCT/US97/17485, filed on Sep. 30, 1997.

(51) Int. Cl.[7] .............................................. A61K 39/395
(52) U.S. Cl. ................. 424/143.1; 424/130.1; 424/138.1; 424/139.1
(58) Field of Search ........................... 424/184.1, 130.1, 424/138.1, 143.1, 139.1

(56) References Cited

U.S. PATENT DOCUMENTS 5,766,591 A * 6/1998 Brooks et al.

OTHER PUBLICATIONS

Fabbri et al. (Tissue Antigens, vol. 48, 1996, pp. 47–51).*

* cited by examiner

*Primary Examiner*—Anthony C. Caputa
*Assistant Examiner*—Gary B. Nickol
(74) *Attorney, Agent, or Firm*—David Prashker

(57) ABSTRACT

The present invention provides a method for inhibiting tumor angiogenesis in a living subject. The method relies upon tumor angiogenesis mediated by vascular endothelial growth factor and specified induced integrin cell surface receptors expressed on the endothelial cells of tumor-included and tumor-associated blood vessels. The methodology also administers at least one antagonistic preparation effective against specified induced and expressed integrin heterodimers on the endothelial cell surface of the living subjects, the consequence of which results in an effective inhibition of tumor angiogenesis in-vivo.

7 Claims, 18 Drawing Sheets

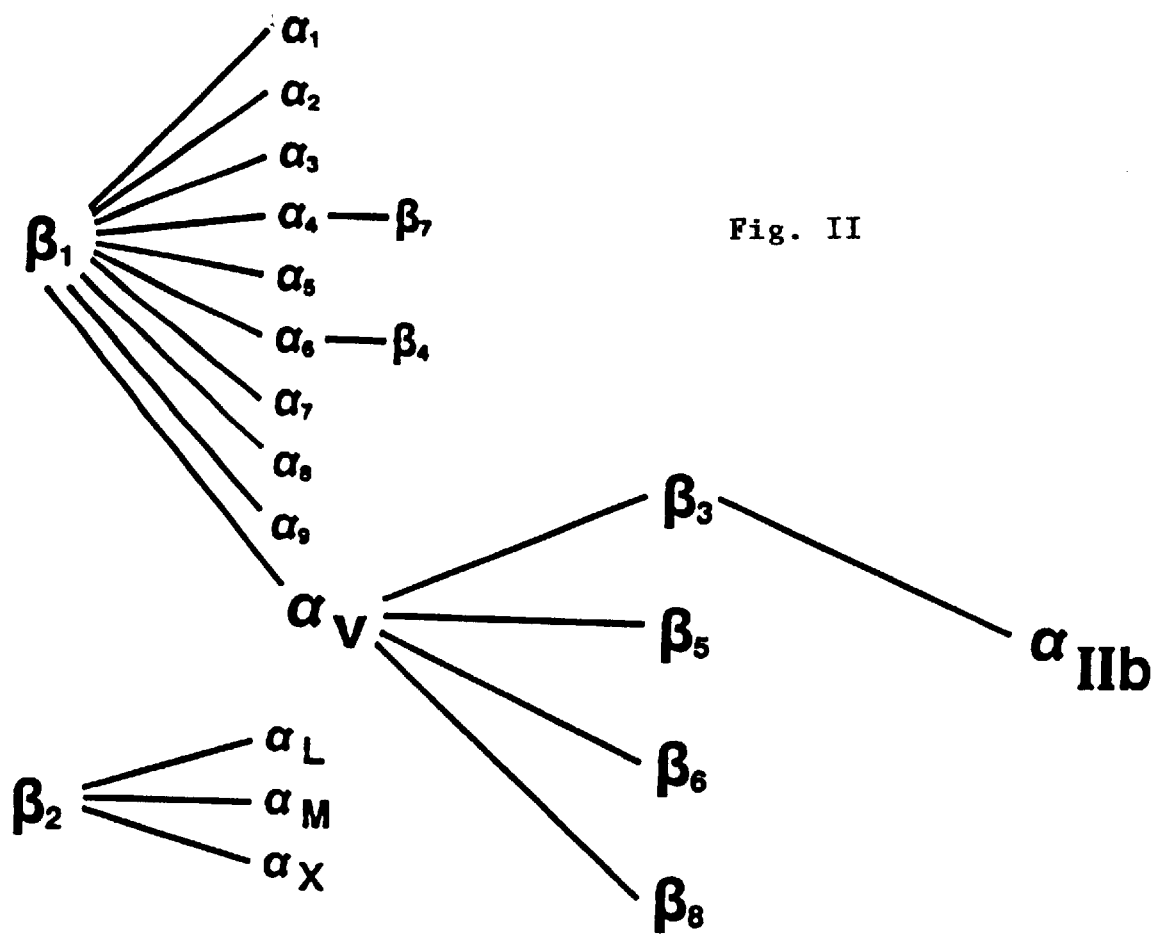
Fig. II

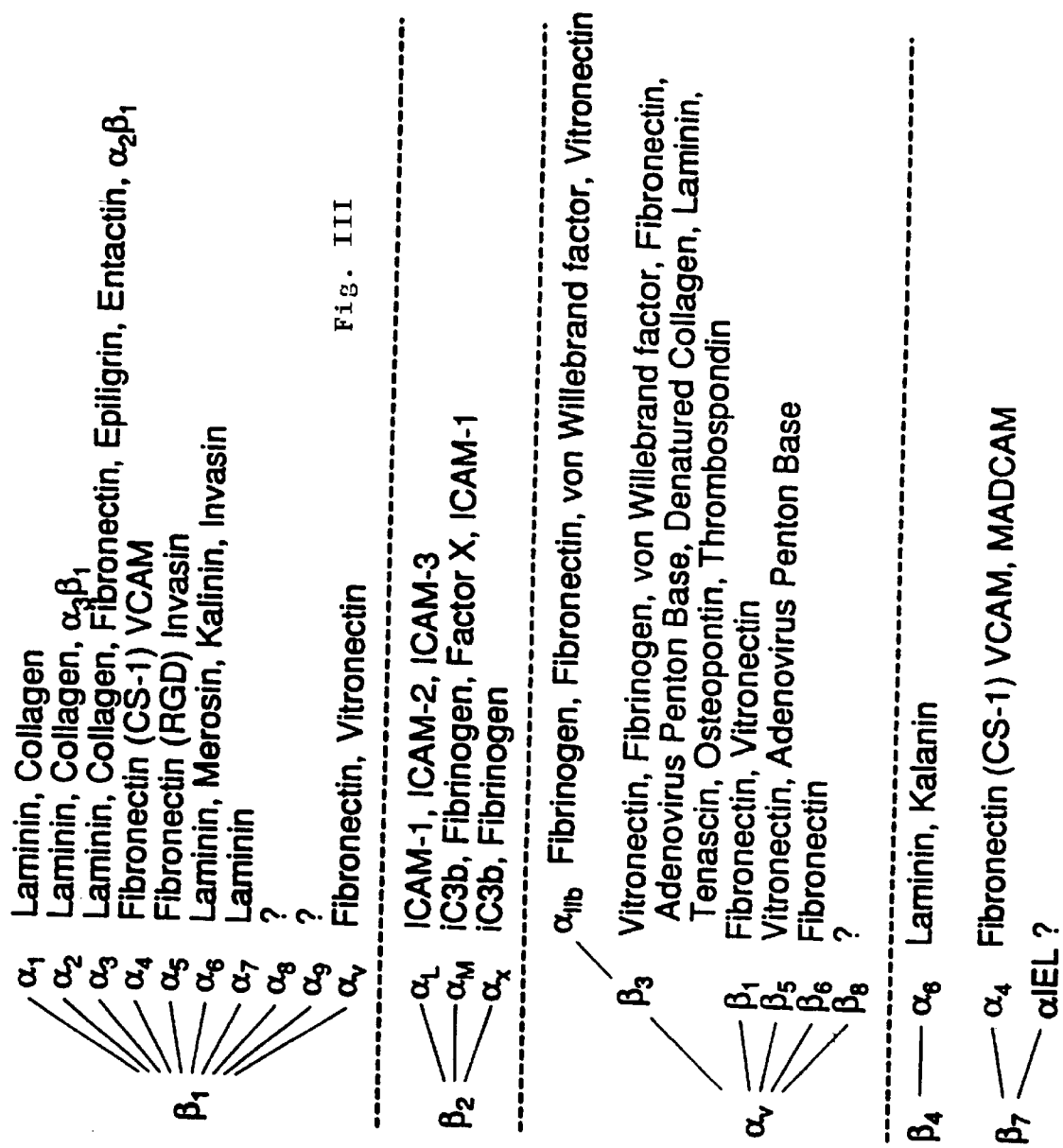
Fig. III

```
VEGF121   -26  MNFLLSWVHWSLALLLYLHHAKWSQAAPMAEGGGQNHHEVVKFMDVYQRS
VEGF165   -26  MNFLLSWVHWSLALLLYLHHAKWSQAAPMAEGGGQNHHEVVKFMDVYQRS
VEGF189   -26  MNFLLSWVHWSLALLLYLHHAKWSQAAPMAEGGGQNHHEVVKFMDVYQRS
VEGF206   -26  MNFLLSWVHWSLALLLYLHHAKWSQAAPMAEGGGQNHHEVVKFMDVYQRS

VEGF121    25  YCHPIETLVDIFQEYPDEIEYIFKPSCVPLMRCGGCCNDEGLECVPTEES
VEGF165    25  YCHPIETLVDIFQEYPDEIEYIFKPSCVPLMRCGGCCNDEGLECVPTEES
VEGF189    25  YCHPIETLVDIFQEYPDEIEYIFKPSCVPLMRCGGCCNDEGLECVPTEES
VEGF206    25  YCHPIETLVDIFQEYPDEIEYIFKPSCVPLMRCGGCCNDEGLECVPTEES

VEGF121    75  WITMQIMRIKPHQGQHIGEMSFLQHNKCECRPPKDRARGEK---------
VEGF165    75  WITMQIMRIKPHQGQHIGEMSFLQHNKCECRPPKDRARGEK---------
VEGF189    75  WITMQIMRIKPHQGQHIGEMSFLQHNKCECRPPKKDRARGEKKSVRGKGGR
VEGF204    75  WITMQIMRIKPHQGQHIGEMSFLQHNKCECRPKKDRARGEKKSVRGKGGR
```

FIG. 1A

```
VEGF121     ----------------------------------------
VEGF165     --------------------------PCGPCSERRKHLFVQDPQ
VEGF189 125 QKRKRKKSRYKSWSV-----------PCGPCSERRKHLFVQDPQ
VEGF204 125 QKRKRKKSRYKSWSVYVGARCCLMPWSLPGPHPCGPCSERRKHLFVQDPQ

VEGF121     ----------------------------CDKPRR        [SEQ ID NO:1]
VEGF165 134 TCKCSCKNTDSRCKAROLELNERTCRCDKPRR           [SEQ ID NO:2]
VEGF189 158 TCKCSCKNTDSRCKAROLELNERTCRCDKPRR           [SEQ ID NO:3]
VEGF204 175 TCKCSCKNTDSRCKAROLELNERTCRCDKPRR           [SEQ ID NO:4]
```

FIG. 1B

```
MVPRRPASLEVTVTVACIWLLTVILGFCVSFNVd
VKNSMTFSGPVEDMFGYTVQQYENEEGKWVLIGS
PLVGQPKN*RTGDVYKCPVGRGESLPCVKLDLPVN*
TSIPN*VTEVKEN*MTFGSTLVTNPNGGFLACGPLY
AYRCGHLHYTTGICSDVSPTFQVVNSIAPVQEC*S
TQLDIVIVLDGSNSIYPMDSVTA    LNDLLKRMD

```
FEMEMSQTGFSAHYSQDMVWLGAVGAYDWN*GTVV

NQKASQIIIPRN*TTFNVESTKKNEPLASYLGYTV

NSATASSGDVLYIAGQPRYN*HTGQVIIYRMEEGN

IKILQTLSGEOIGSYFGSILTTTDIDKDSNTDIL

LVGAPMYMGTEKEEGGKVYYYALN*QTRFEYQMSL

APMEPIKQTCCSSRQHNSCTTENKNEPCGARFGTAIA

AVKDLNLDGFNDIVIGAPLEDDHGGAVYIYHGSG

KTIRKEYAORIPSGGDGKTLKFFGQSIHGEMDLN

GDGLTDVTICGLGGAALFWSRDVAVVKVTMNFEP

NKVNIQKKNCHMEGKETVCIN*ATVCFEVKLKSKE

DTIYEADLQYRVTLDSLRQISRSFFSGTQERKVQ

RN*ITVRKSECTKHSFYMLDKHDFQDSVRITLDFN*
```

FIG. 2B

LTDPENGPVLDDSLPNSVHEYIPFAKDCGNKEKC

ISDLSLHVATTEKDLLIVRSQNDKFN*VSLTVKNT

KDSAYNTRTIVHYSPNLVFS GIEAIQKDSCESNH

N*ITCKVGYPFLRRGEMVTFKILFQFN*TSYLMEN*V

TIYLSATSDSEEPP ETLSDNVVN*ISIPVKYEVGL

QFYSSASEYHISIAAN*ETVPEVIN*STEDIGNEIN

IFYLIRKSGSFPMPELKLSISFPN*MTSNGYPVLY

PTGLSSSENANCRPHIFEDPFSINSGKKMTT STD

HLKRGTILDCNTCKFATITCN*LTSSDISOVN*VSL

ILWKPTFIKSYFSSLN*LTIRGELRSEN*ASLVLSS

SNQKRELAIQISKDGLPGRVPLWVILLSAFAGLL

LLMLLILALWKIGFFKRPLKKKMEK [SEQ ID NO:5]

FIG. 2C

```
                                          -12
MGPERTGAAPLPLLLVLA

23
LSQGILNCCLAYNVGLPEAKIFSGPSSEQFGYAV

57
QQFINPKGNWLLVGSPWSGFPENRMGDVYKCPVD

91
LSTATCEKLNLQTSTS*PN*VTEMKTN*MSLGLILT

125
RNMGTGGFLTCGPLWAQQCGNQYYTTGVCSDISP

159
DFQLSASFSPATQPCPSLIDVVVVCDESNSIYP W

193
DAVKNFLEKFVQGLDIGPTKTQVGLIQYANNPRV

227
VFNLNTYKTKEEMIVATSQTSQYGGDLTNTFGAI

261
QYARKYAYSAASGGRRSATKVMVVTDGESHDGS

295
MLKAVIDQCNHDNILRFGIAVLGYLNRNALDTKMN

329
LIKEIKAIASIPTERYFFN*VSDEAALLEKAGTLG

363
EQIFSIEGTVQGGDNFQMEM SQVGFSADYSSQND

397
ILMLGAVGAFGWSGTIVQKTSHGHLIFPKQAFDQ
```

FIG.3A

```
IQDRN*HSSYLGYSVAAISTGESTHFVAGAPRAN*                      431
VTGQIVLYSVNENGN*ITVIQAHRGDQIGSYFGSV                      465
LCSV[DVDKDTITD]VLLVGAPMYMSDLKKEEGRVY                     499
LFTIKKGILGQHQFLEGPEGIENTRFGSAIAALS                       533
[DINMDGFND]VIVGSPLENQNSGAVVIYNGHQGTI                     567
RTKYSQKILGSDGAFRSHLQYFGRSLDGYG[DLNG]                     601
[DSITD]VSIGAFGQVVQLWSQSIADVAIEASFTPE                     635
KITLVNKNAQIILKLCFSAKFRPTKQNNQVAIVY                       669
N*ITLDADGFSSRVTSRGLFKENNERCLQKNMVVN                      703
QAQSCPEHIIYIQEPSDVVNSLDDLRVDISLENPG                      737
TSPALEAYSETAKVFSIPFHKDCGEDGLCISDLV                       771
LQDVRIPAAQEQPFIVSNQNKRLTFSVTLKNKRE                       805
```

FIG. 3B

```
SAYNTGIVVDFSENLFFASFSLPVDGTEVTCQVA            839
ASQKSVACDVGYPALKREQQVTFTINFDFNLQNL            873
QNQASLSFQALSESQEENKADNLVNLKIPLLYDA            907
EIHLTRSTNINFYEISSDGNVPSIVHSFEDVGPK            941
FIFSLKVTTGSVPVSMATVIIHIPQYTKEKNPLM            975
YLTGVQTDKAGDICCNADINPLKIGQTSSSVSFK            1009
SENFRHTKELNCRTASCSN*VTCWLKDVHMKGEYF           1043
VN*VTTRIWN*GTFASSTFQTVQLTAAAEINTYNPE          1077
IYVIEDNTVTIPLMIMKPDEKAEVPTGVIIGSII            1111
AGILLLLALVAILWKLGFFKRKYEKMTKKNPDEID           1145
ETTELSS [SEQ ID NO:6]                         1152
```

FIG. 3C

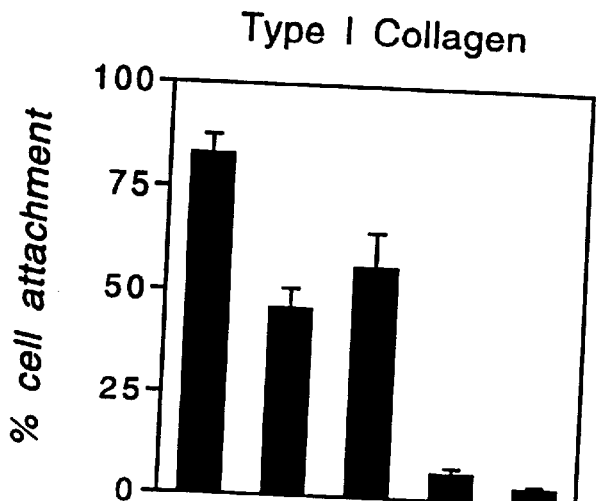
Fig. 6A
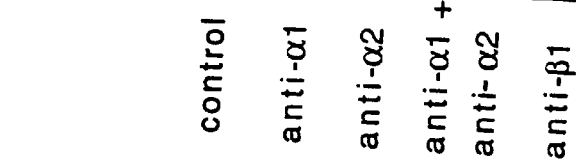
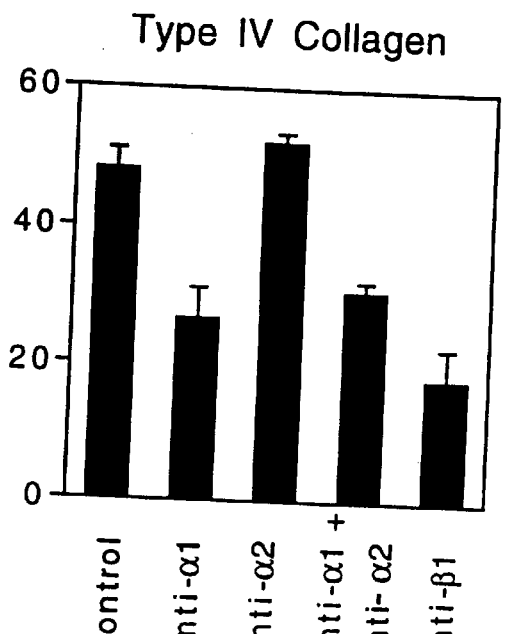
Fig. 6B
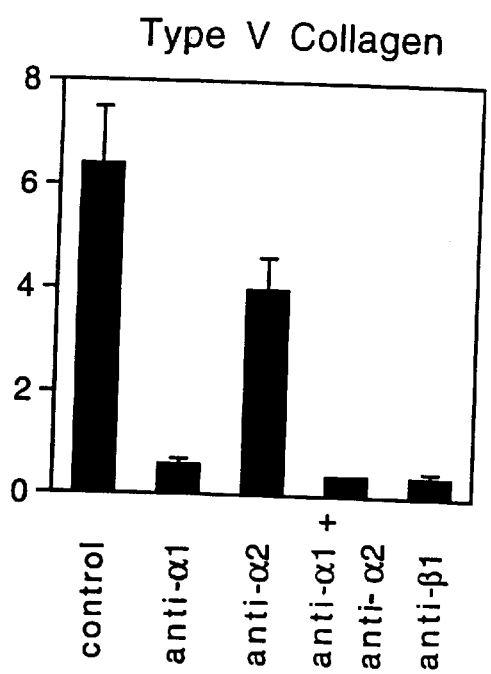
Fig. 6C

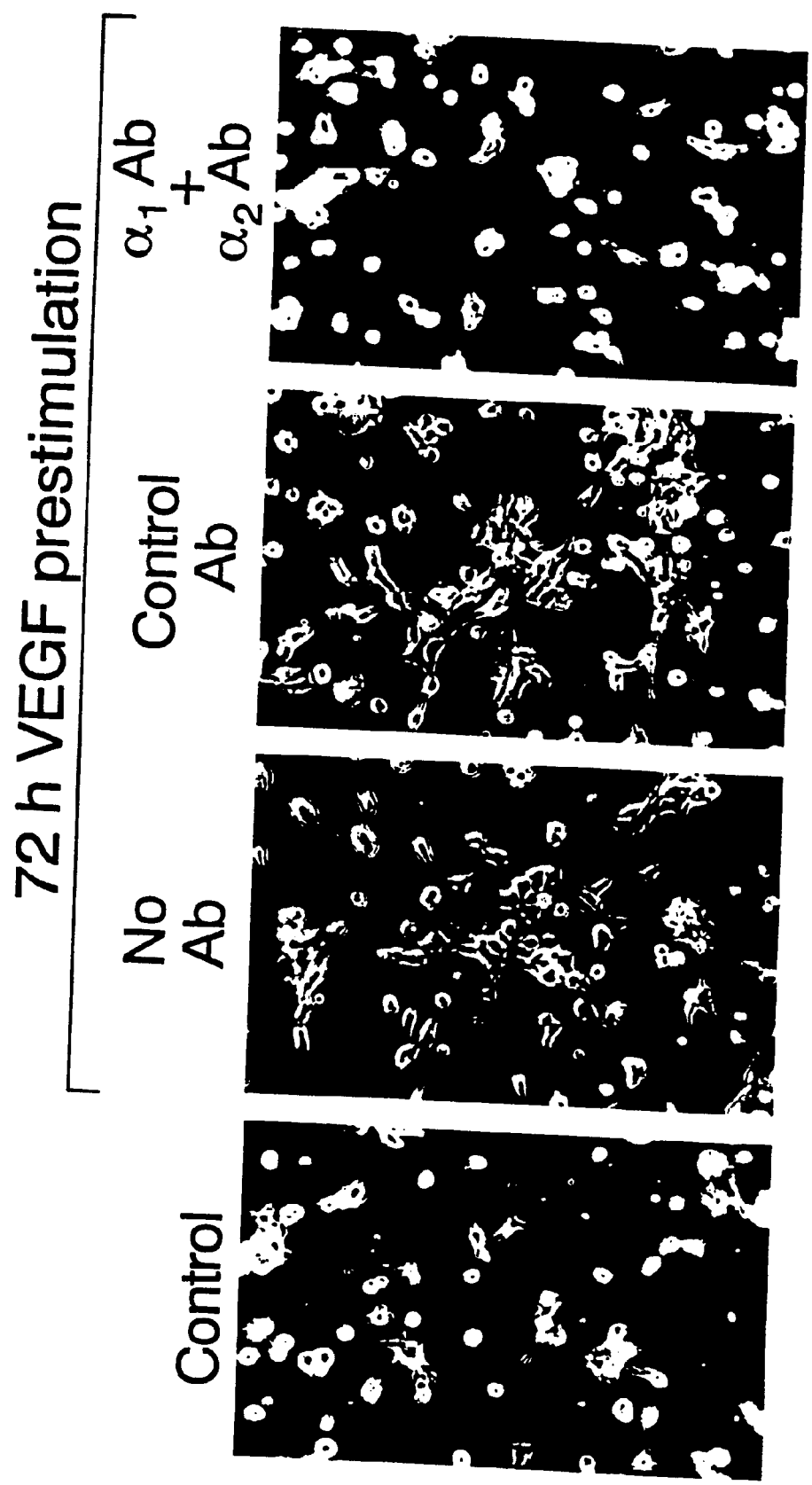

METHOD FOR INHIBITING TUMOR ANGIOGENESIS IN A LIVING SUBJECT

This application is a continuation of international application number PCTUS97/17485, filed Sep. 30, 1997, now pending.

FIELD OF THE INVENTION

The present invention is concerned with angiogenesis broadly and with tumor angiogenesis directly; and is focused on means and methods for inhibiting tumor angiogenesis involving vascular endothelial growth factor ("VEGF") and integrin heterodimer surface receptors found in the vasculature of a living subject.

BACKGROUND OF THE INVENTION

Angiogenesis, the formation of new capillaries and blood vessels, is a complex process first recognized in studies of wound healing and then with investigations of experimental tumors. Angiogenesis involves extracellular matrix remodeling, endothelial cell migration and proliferation, and functional maturation of endothelial cells into mature blood vessels [Brier, G. and K. Alitalo, *Trends Cell Biol.* 6: 454–456 (1996)]. Although the process generally has been studied for more than 50 years, the existence and in-vivo effects of several discrete angiogenic factors have been identified just over a decade ago [Folkman, J. and M. Klagsburn, *Science* 235: 444–447 (1985)]. Clearly, in normal living subjects, the process of angiogenesis is a normal host response to injury; and as such is an integral part of the host body's homeostatic mechanisms.

In distinction, tumor angiogenesis is the specific development in-vivo of an adequate blood supply for a solid tumor mass; and the growth of a tumor in-vivo beyond the size of a few millimeters in diameter is believed to be dependent upon the existence, maintenance, and continued development of sufficient and functional blood vasculature in-situ. In a variety of experimental tumor systems, tumor survival and growth has been linked with new capillary and new blood vessel formation. Histological examination of such neoplasms has revealed that tumor cells typically surround blood capillaries in a cylindrical configuration with a radius not exceeding about 200 micrometers—the critical travel distance for diffusion of molecular oxygen [Folkman, J., *Cancer Res.* 46: 467–473 (1986)]. Moreover, in the cancer patient, tumor angiogenesis originates at least in part from the sprouting of new capillaries and blood vessels directly from the pre-existing and functional normal vasculature; and possibly also from stem cells existing in the blood. Tumor angiogenesis thus involves endothelial cell penetration of the vascular basement membrane in a preexisting blood vessel; followed by endothelial cell proliferation; and then by an invasion of the extracellular matrix surrounding the blood vessel to form a newly created vascular spout [Vernon, R. and E. H. Sage, *Am. J. Pathol.* 147: 873–883 (1995); Auspunk, D. H. and J. Folkman, *Microvasc. Res.* 14: 53–65 (1977)].

A number of different biologically active and physiologically functional molecular entities appear to be individual factors of angiogenesis. Among these are the biologically active classes of substances known as vascular endothelial growth factor and the integrin protein family of cell surface receptors. Each of these two classes will be summarily reviewed as to their conventionally known properties and functions.

Vascular Endothelial Growth Factor

Vascular endothelial growth factor (hereinafter "VEGF"), also known as vascular permeability factor, is a 34–45 kilodalton dimeric glycoprotein; is a cytokine; and is a potent inducer of microvascular hyperpermeability. As such, VEGF is believed to be responsible for the vascular hyperpermeability and consequent plasma protein-rich fluid accumulation that occurs in-vivo with solid tumors and ascites tumors [Senger et al., *Science* 219: 983–985 (1983); Dvorak et al., *J. Immunol.* 122: 166 (1979); Nagy et al., *Biochem. Biophys. Acta.* 948: 305 (1988); Senger et al., *Federation Proceedings* 46: 2102 (1987)]. On a molar basis, VEGF increases microvascular permeability with a potency which is typically 50,000 times that of histamine [Senger et al., *Cancer Res.* 50: 1774–1778 (1990)].

Vascular endothelial growth factor is also noted for its mitogenic effects on vascular endothelial cells (hereinafter "EC"). VEGF is a specific EC mitogen which stimulates endothelial cell growth and promotes angiogenesis in-vivo [Conn et al., *Proc. Natl. Acad. Sci. USA* 87: 2628–2632 (1990); Ferrara et al., *Biochem. Biophys. Res. Comm.* 161: 851–858 (1989); Gospodarowicz et al., *Proc. Natl. Acad. Sci. USA.* 86: 7311–7315 (1989); Keck et al., *Science* 264: 1309 (1989); Leung et al., *Science* 246: 1306 (1989); Connolly et al., *J. Clin. Invest.* 84: 1407–1478 (1989)]. In addition, VEGF exerts a number of other effects on endothelial cells in-vitro. These include: an increase in intracellular calcium; a stimulation of inositol triphosphate formation; a provocation of von Willebrand factor release; and a stimulation of tissue factor expression [Brock et al., *Am. J. Pathol.* 138: 213 (1991); Clauss et al., *J. Exp. Med.* 172: 1535 (1990)].

Vascular endothelial growth factor elicits potent angiogenic effects by stimulating endothelial cells through two receptor tyrosine kinases, Flt-1 and KDR/Flk-1 [Dvorak et al., *Am. J. Pathol.* 146: 1029–1039 (1995); Mustonen, T. and K. Alitalo, *J. Cell Biol.* 129: 895–898 (1996)]. Although there are potentially numerous angiogenesis factors, considerable evidence has accumulated indicating that VEGF is a cytokine of importance both for neovascularization in the medically normal adult and for development of embryonic vasculature. VEGF angiogenic activity has been demonstrated in several experimental models including the chick chorioallantoic membrane [Whiting et al., *Anat. Embryol.* 186: 251–257 (1992)]; rabbit ischemic hind limb [Takeshita et al., *J. Clin. Invest.* 93: 662–670 (1994)]; tumor xenografts in mice [Potgens et al., *Biol: Chem. Hoppe. Seyler* 376: 57–70 (1995); Claffey et al., *Cancer Res.* 56: 172–181 (1996)]; and a primate model of iris neovascularization [Tolentino et al., *Arch. Ophthalmol.* 114: 964–978 (1996)]. Additionally, both infusion of exogenous VEGF and overexpression of VEGF endogenously were found to induce hypervascularization of avian embryos [Drake et al., *Proc. Natl. Acad. Sci. USA* 92: 7657–7661 (1995); Flamme et al., *Dev. Biol.* 171: 399–414 (1995)].

Evidence supporting the importance of VEGF for angiogenesis generally also has come from analyses of VEGF and VEGF receptor expression. These investigations have established that elevated expression of VEGF and its receptors correlate both temporally and spatially with vascularization during embryogenesis [Millauer et al., *Cell* 72: 835–846 (1993); Peters et al., *Proc. Natl. Acad. Sci. USA* 90: 8915–8919 (1993)]; and also with the angiogenesis associated with wound healing [Brown et al., *J. Exp. Med.* 176: 1375–1379 (1992)]; cancer [Brown et al., *Cancer Res.* 53: 4727–4735 (1993)]; rheumatoid arthritis [Fava et al., *J. Exp. Med.* 180: 341–346 (1994)]; psoriasis [Detmar et al., *J. Exp.*

Med. 180: 1142–1146(1994)]; delayed-type hypersensitivity reactions [Brown et al., J. Immunol. 154: 2801–2807 (1995)]; and proliferative retinopathies [Aiello et al., N. Eng. J. Med. 331: 1480–1487 (1994); Pierce et al., Proc. Natl. Acad. Sci. USA 92: 905–909 (1995)]. Thus, VEGF appears not only to promote angiogenesis in a variety of experimental systems, but also appears to be overexpressed in a diversity of settings in which neovascularization is prominent.

VEGF is typically synthesized and secreted in-vivo by a variety of cultured tumor cells, transplantable animal tumors, and many different primary and metastatic human tumors [Dvorak et al., J. Exp. Med. 174: 1275–1278 (1991); Senger et al., Cancer Res. 46: 5629–532 (1986); Plate et al., Nature 359: 845–848 (1992); Brown et al., Am. J. Pathol. 143: 1255–1262 (1993)]. Solid tumors, however, must generate a vascular stroma in order to grow beyond a minimal size [Folkman, J. and Y. Shing, J. Biol. Chem. 267: 10931–10934 (1992)].

VEGF today is believed able to be a central mediator of angiogenesis generally as well as of tumor angiogenesis in particular. Monoclonal antibody directed against VEGF has been shown to suppress growth and decrease the density of blood vessels in experimental tumors [Kim et al., Nature 362: 841–844 (1993)].

It will be noted and appreciated also that many research investigations reported in the scientific and patent literature have employed antibodies raised against VEGF in order to identify and characterize the functions, properties, and attributes of the VEGF molecule in-vivo. Merely illustrating the range and variety of these investigations and published reports are the following: Preparation of specific antibodies [U.S. Pat. No. 5,036,003]; use of monoclonal antibodies to suppress growth and decrease density of blood vessels in tumors [Kim et al., Nature 362: 841–844 (1 993)]; inhibition of tumor growth and metastasis by antibody to VEGF [Asano et al., Cancer Res. 55: 5296–5301 (1995)]; inhibition of VEGF activity with specific antibodies [Sioussat et al., Arch. Biochem. Biophys. 301: 15–20 (1993)]; the structure of solid tumors and their vasculature [Dvorak et al., Cancer Cells 3: 77–85 (1993)]; and the distribution of VEGF in tumors and the concentration of VEGF in tumor blood vessels [Dvorak et al., J. Exp. Med. 174: 1275–1278 (1991)]. The text of each and all of these cited publications concerning VEGF is expressly incorporated by reference herein.

The Integrin Protein Family

Integrins are a specific family of cell surface receptors which function in-vivo as adhesive molecules for a large variety of different compounds and ligands. As a member of this specific receptor family, each integrin entity chemically is a heterodimeric glycoprotein; and is structurally composed of two different non-covalently linked protein subunits, each of the individual subunit moieties being chosen from among the alternative members forming a discrete 130–210 kilodalton "alpha" ($\alpha$) subunit group and the individual members forming another distinct 95–130 kilodalton "beta" ($\beta$) subunit group. The overall structure of an integrin receptor molecule generally is illustrated by FIG. A [reproduced from Hynes, R. O., Cell 48: 549–554 (1987); see also Springer, T. A., Fed. Proc. 44: 2660–2055 (1985); Hynes, R. O., Cell 69: 11–25 (1992); Ruoslahti et al., Kidney Internatl. 45: S17–S22 (1994); and INTEGRINS: Molecular and Biological Responses to the Extracellular Matrix, (Cheresh & Mecham, editors), Academic Press, 1994.

As seen in FIG. A, the alpha and beta subunits are joined in a non-covalent linkage to form a unitary whole—i.e., the heterodimer. Each subunit has a transmembrane segment (shown in FIG. A as a dark area); a small C-terminal cytoplasmic domain (shown in FIG. A as a stippled area); and a large N-terminal extracellular domain. The beta ($\beta$) subunits as a group typically contain sequences of extensive intrachain disulphide bonding, including four repeated regions of a forty amino acid cysteine-rich segment (shown in FIG. A as a crosshatched area). Also, some alpha ($\alpha$) subunit members of the group are cleaved posttranslationally to provide a heavy chain and a light chain linked by internal disulphide bonding to form the complete subunit entity. For a more detailed description of the integrin molecular structure, see Hynes, R. O., Cell 48: 549–554 (1987) and the references cited therein; Hynes, R. O., Cell 69: 11–25 (1992); Ruoslahti et al., Kidney Internatl. 45: S17–S22 (1994); and INTEGRINS: Molecular and Biological Responses to the Extracellular Matrix, (Cheresh & Mecham, editors), Academic Press, 1994.

It is essential to recognize also that each alpha subunit group and each beta subunit group has its own distinctive members, each of which can become non-covalently linked to more than one member of the corresponding subunit type. At present, the alpha subunit group comprises not less than fourteen (14) different entities; while the beta subunit group comprises not less than eight (8) different members. A representative listing and correlation of the presently recognized possible combinations and permutations of individual $\alpha$ and $\beta$ subunits is shown by FIG. B. [reproduced in part from INTEGRINS: Molecular And Biological Responses to the Extracellular Matrix, (Cheresh & Mecham, editors), Academic Press, 1994, (preface page xii)].

The recognized biological role and in-vivo function of the integrin protein family are as cell surface receptors for cell-to-cell or cell-to-matrix interactions. Many of the individual integrin heterodimers comprising the family as a whole were first identified by their ability to bind with one specific ligand or matrix glycoprotein extracellularly. In this manner, the individual integrin heterodimers (each comprised of different $\alpha$ and $\beta$ subunits) have demonstrated a variety of unique and alternative specific binding affinities and capacities for a diverse range of singular extracellular ligands in-vivo. The conventionally known range of such extracellular ligands presently includes: laminin, collagen, fibronectin, vitronectin, epiligin, entactin, merosin, kalinin, invasin, tenascin, osteopontin, thrombospondin, adenovirus penton base, intercellular adhesion molecule-1 (ICAM-1), vascular cell adhesion molecule-1 (VCAM-1), and von Willebrand factor. A representative listing of the individual $\alpha$ and $\beta$ subunits composing the integrin unit with the corresponding specific bind affinity ligand is presented by FIG. C [also reproduced in part from INTEGRINS: Molecular and Biological Responses to the Extracellular Matrix, (Cheresh and Mecham, editors), Academic Press, 1994, (preface page xii)].

In addition, for the purposes of clarity and avoidance of misunderstandings or ambiguities, it is necessary to note and appreciate that the reported research investigations of what are now recognized as integrin protein molecules were pursued by different persons working in different scientific fields for a variety of different purposes. As an unfortunate consequence of this historical development of the integrin field, a series of different and alternative titles were originally given and applied to substances thought first to be different—but which were subsequently found to be a single chemical structure and composition alone. This multiple naming and title designation occurrence was recognized in the literature very early; and a major effort was undertakenby 1987 to reconcile the various designations into a more consistent and uniform naming system, as is exemplified by Table 1 below [reproduced from Hynes, R. O., *Cell* 48: 549–554 (1987)]. Thus, as Table 1 shows, the $\alpha_1\beta_1$ integrin molecule was also known in 1987 as "human very late activation protein 1 complex" or VLA-1. Similarly, the $\alpha_2\beta_1$ integrin unit in 1987 was also alternatively titled "platelet membrane glycoprotein Ia-IIa complex" or GPIa/IIa; and as "human very late activation protein 2 complex" or VLA-2; and also as "fibroblast extracellular matrix receptor II", a misnomer of its true binding affinity (as shown by FIG. C).

The $\beta$ subunit grouping in particular appears to have become a favored target of current research efforts. Thus, for example, cyclic peptide compounds have been developed which can inhibit $\beta_1$ and $\beta_2$ mediated adhesion [PCT Int. Pub. No. WO 96/40781 dated Dec. 19, 1996]. Also, the function of the arginine-glycine-aspartic acid (RGD) amino acid sequence as a specific recognition sequence within ligands binding to $\beta_3$ subunits has been the focus of several different recent innovations and novel peptide compounds. [PCT Int. Pub. No. WO 97/08203 dated Mar. 6, 1997; PCT Int. Pub. No. WO 97/14716 dated Apr. 24, 1997; see also U.S. Pat. Nos. 5,192,746; 5,294,713; and 5,260,277.]

TABLE 1

Members of the Integrin Receptor Family

| | Subunit Molecular Weight ($\times 10^{-3}$) | | Probable Subunit | | |
|---|---|---|---|---|---|
| | Nonreduced | Reduced | Composition | Known Ligands | Known Functions |
| Chicken integrin complex[a] | 155/135/120 | 155/130/125 | $\alpha_0\beta_1$ $\alpha_3\beta_1$ | FN, LM, VN | Cell adhesion, cell migration Cytoskeletal connection |
| Fibronectin receptor | 160/120 | 150/130 | $\alpha_F\beta_1$ | FN | Adhesion to fibronectin |
| Vitronectin receptor | 160/100 | 135[b]/115 + 25 | $\alpha_V\beta_3$ | VN | Adhesion to vitronectin |
| Glycoprotein IIb/IIIa | 142/95 | 130[c]/105 + 23 | $\alpha_{IIb}\beta_3$ | FN, FB, VN, VWF (TSP? Collagen?) | Platelet adhesion and aggregation |
| LFA-1 | — | 180/95 | $\alpha_L\beta_2$ | — | Leukocyte adhesion T lymphocyte help, lymphocyte cytotoxicity |
| Mac-1 | — | 170/95 | $\alpha_M\beta_2$ | C3bi | C3b receptor Monocyte and neutrophil adhesion |
| p150,95 | — | 150/95 | $\alpha_X\beta_2$ | C3bi | Neutrophil adhesion |
| VLA-1 | 200/110 | 210/130 | $\alpha_1\beta_1$ | — | |
| VLA-2 | 150/110 | 165/130 | $\alpha_2\beta_1$ | — | |
| VLA-3 | 150/110 | 135/130 | $\alpha_3\beta_1$ | — | |
| VLA-4 | 140/110 | 150/130 | $\alpha_4\beta_1$ | — | |
| VLA-5 | 150/110 | 130/130 | $\alpha_F\beta_1$ | — | |

[a]Also known as 140K complex, CSAT antigen, JG22 antigen.
[b,c]These $\alpha$ chains consist of a heavy and a light chain held together by disulfide bonding.
The molecular weights are from different publications (see text for references) and thus may not be exactly comparable. Abbreviations for ligands are: FN, fibronectin; LM, laminin; VN, vitronectin; FB, fibrinogen; VWF, von Willebrand factor; TSP, thrombospondin; C3bi, inactivated form of C3b component of complement. The probable subunit composition of each receptor and the suggested nomenclature for $\beta$ subunits are discussed in the text. A tentative nomenclature suggested for $\alpha$ chains is as follows. Those with well-defined ligands are denoted by the first letter of the ligand (e.g., $\alpha_F$, fibronectin; $\alpha_V$, vitronectin). Others are denoted by the first letter of the original cell type ($\alpha_L$, leukocyte; $\alpha_M$, macrophage) or, where no simple designation exists, by the numbers or letters used by the authors. In the case of $\alpha$ subunits are posttranslationally cleaved (e.g., $\alpha_{IIb}$, $\alpha_V$, and possibly $\alpha_0$, $\alpha_3$, $\alpha_4$), it is suggested that the heavy and light chains be denoted by superscripts (e.g., IIb$\alpha$ = $\alpha_{IIb}^H$ and IIb$\beta$ = $\alpha_{IIb}^L$). It is possible that some of the $\alpha$ chains listed could be identical with others and that other $\alpha$ chains exist. These ambiguities may necessitate future changes in nomenclature.

The integrin protein family as a whole, being cell surface receptors for specific extracellular matrix ligands, has been implicated in the processes of extracellular matrix remodeling, in endothelial cell migration, and in the function maturation of new endothelial cells into mature blood vessels—the complex process of angiogenesis generally. See for example, Hynes, R. O., *Cell* 69: 11–25 (1992); Ruoslahti et al., *Kidney Internatl.* 45: S17S22 (1994); and Schwartz et al., *Ann. Rev. Cell Dev. Biol.* 11: 549599 (1995). Also published reports of targeted gene deletion of $\alpha_5$ and $\alpha v$ integrin subunits in living mice apparently resulted in embryonic vascular defects [Hynes, R. O., *Develop. Biol.* 180: 402–412 (1996)]; and an antibody which broadly inhibited members of the $\beta_1$ subunit was shown to inhibit development of the embryonic vasculature [Drake et al., *Develop. Dyn.* 193: 83–91 (1992)].

In addition, other reported investigations employing a variety of different experimental models have demonstrated that an inhibition of tumor angiogenesis and of normal vasculature development can be achieved using an anti-$\alpha_v\beta_3$ blocking antibody [Brooks et al., *Science* 264: 569–571 (1994); Brooks et al., *Cell* 79: 1157–1164 (1994), Brooks et al., *J. Clin. Invest.* 96: 1815–1822 (1995); Drake et al., *J. Cell Sci.* 108: 2655–2661 (1995)]; as well as by using an ant-$\alpha_v\beta_5$ blocking antibody [Friedhandler et al., *Science* 270: 1500–1502 (1995)].

To illustrate the general state of the pertinent field and to provide a greater degree of descriptive detail generally regarding conventionally known properties, capabilities and chemical composition and structure for the alpha ($\alpha$) subunit group and membership; the beta ($\beta$) subunit group and membership; and the integrin protein family as a whole—the reader is directed to the following representative publications, all of which are also expressly incorporated by reference herein: Santoro, S. A., *Cell* 46: 913–920 (1986); Mould et al., *J. Biol. Chem.* 265: 4020–4024 (1989); Wagner et al., *J. Cell Biol.* 109: 1321–1220 (1989); Guan, J. L. and R. O. Hynes, *Cell* 60: 53–61 (1990); Staaz et al., *J. Biol. Chem.* 265: 4778–4781 (1990); Carter et al., *J. Cell Biol.* 110: 1387–1404 (1990); Wayner, E. A. and W. G. Carter, *J. Cell Biol.* 105: 1873–1884 (1987); Fitzpatrick et al., *The Structure and Development of Skin,* (Jeffers, Scott & White, editors), McGraw-Hill Co., 1987; Davis et al., *Biochem. Biophys. Res. Comm.* 182: 1025–1031 (1992); Elices, M. J. and M. E. Hemler, *Proc. Natl. Acad. Sci. USA* 86: 9906–9910 (1989); Languino et al, *J. Cell Biol.* 109: 2455–2462 (1989); Takada, Y. and M. E. Hemler, *J. Cell Biol.* 109: 397–407 (1989); Ignatius et al., *J. Cell Biol.* 111: 709–720 (1990); Kirchhofer et al., *J. Biol. Chem.* 265: 615–618 (1990); Kramer et al., *J. Cell Biol.* 111: 1233–1243 (1990); Tawil et al., *Biochemistry* 29: 6540–6544 (1990);

Kern et al., *J. Biol. Chem.* 269: 22811–22816 (1994); Briesewitz et al., *J. Biol. Chem.* 268: 2989–2996 (1993); Sriramarao et al., *J. Cell Sci.* 105: 1001–1012 (1993); Gardner et al., *Develop. Biol.* 175: 301–313 (1996); Wong et al., *Cell Adhesion Commun.* 4: 201–221 (1996); and Mercurio A. M., *Trends Cell Biol.* 5: 419–423 (1995); and Senger et al., *Am. J. Path.* 149: 293–305 (1996).

In sum therefore, despite the very considerable body of presently accumulated information and knowledge regarding vascular endothelial growth factor and the integrin heterodimer family, the relationships or involvements between these two classes of biologically active substances have been explored only minimally to date. Equally important, any respective role or function in-vivo conventionally known for either VEGF or the integrin molecules individually has almost always focused on the properties and capabilities of each class of substance alone and without regard or attention to the possible influence of the other. This perspective and circumstance is true for angiogenesis broadly as well as for tumor angiogenesis in particular. For these reasons accordingly, were an effective and reliable method to be developed for an inhibition of tumor angiogenesis which utilized and depended upon a direct and dependent relationship in-vivo between VEGF and specifically induced and expressed integrin cell surface receptors—such an inhibitory methodology would be recognized and appreciated as an unforeseen and uncontemplated innovation by workers in this technical field.

SUMMARY OF THE INVENTION

The present invention has multiple aspects and alternative definitions. A first aspect of the invention provides a method for inhibiting tumor angiogenesis mediated by vascular endothelial growth factor (VEGF) and integrin cell surface receptors expressed in the vasculature of a living subject, said method comprising the steps of:

allowing mobile VEGF secreted by a tumor mass present within the body of a living subject to become bound in-vivo to the surface of endothelial cells in a tumor-associated blood vessel;

permitting said bound VEGF to induce the expression of specified integrin heterodimers on the endothelial cell surface of the tumor-associated blood vessel in-vivo, said induced and expressed integrin heterodimers being selected from the group consisting of integrins composed of $\alpha_1$ and $\alpha_2$ integrin subunits; and then administering at least one antagonistic antibody preparation effective against said induced and expressed specified integrin heterodimers on the endothelial cell surface to the living subject such that tumor angiogenesis is inhibited in-vivo, said antagonistic preparation comprising at least one antibody specific for an integrin subunit selected from the group consisting of the $\alpha_1$ and $\alpha_2$ integrin subunits.

A second aspect of the invention provides an alternative method for inhibiting tumor angiogenesis mediated by vascular endothelial growth factor (VEGF) and integrin cell surface receptors expressed in the vasculature of a living subject, said alternative method comprising the steps of:

allowing mobile VEGF secreted by a tumor mass present within the body of a living subject to become bound in-vivo to the surface of endothelial cells in a tumor-included blood vessel;

permitting said bound VEGF to induce the expression of specified integrin heterodimers on the endothelial cell surface of the tumor-included blood vessel in-vivo, said induced and expressed integrin heterodimers being selected from the group consisting of integrins composed of $\alpha_1$ and $\alpha_2$ integrin subunits; and then administering at least one antagonistic antibody preparation effective against said induced and expressed specified integrin heterodimers on the endothelial cell surface to the living subject such that tumor angiogenesis is inhibited in-vivo, said antagonistic preparation comprising at least one antibody specific for an integrin subunit selected from the group consisting of the $\alpha_1$ and $\alpha_2$ integrin subunits.

BRIEF DESCRIPTION OF THE FIGURES

The present invention may be more easily understood and completely appreciated when taken in conjunction with the accompanying drawing, in which:

FIG. I is an illustration of the general structure of an integrin heterodimer functional as a cell surface receptor in-vivo;

Figure 4A:
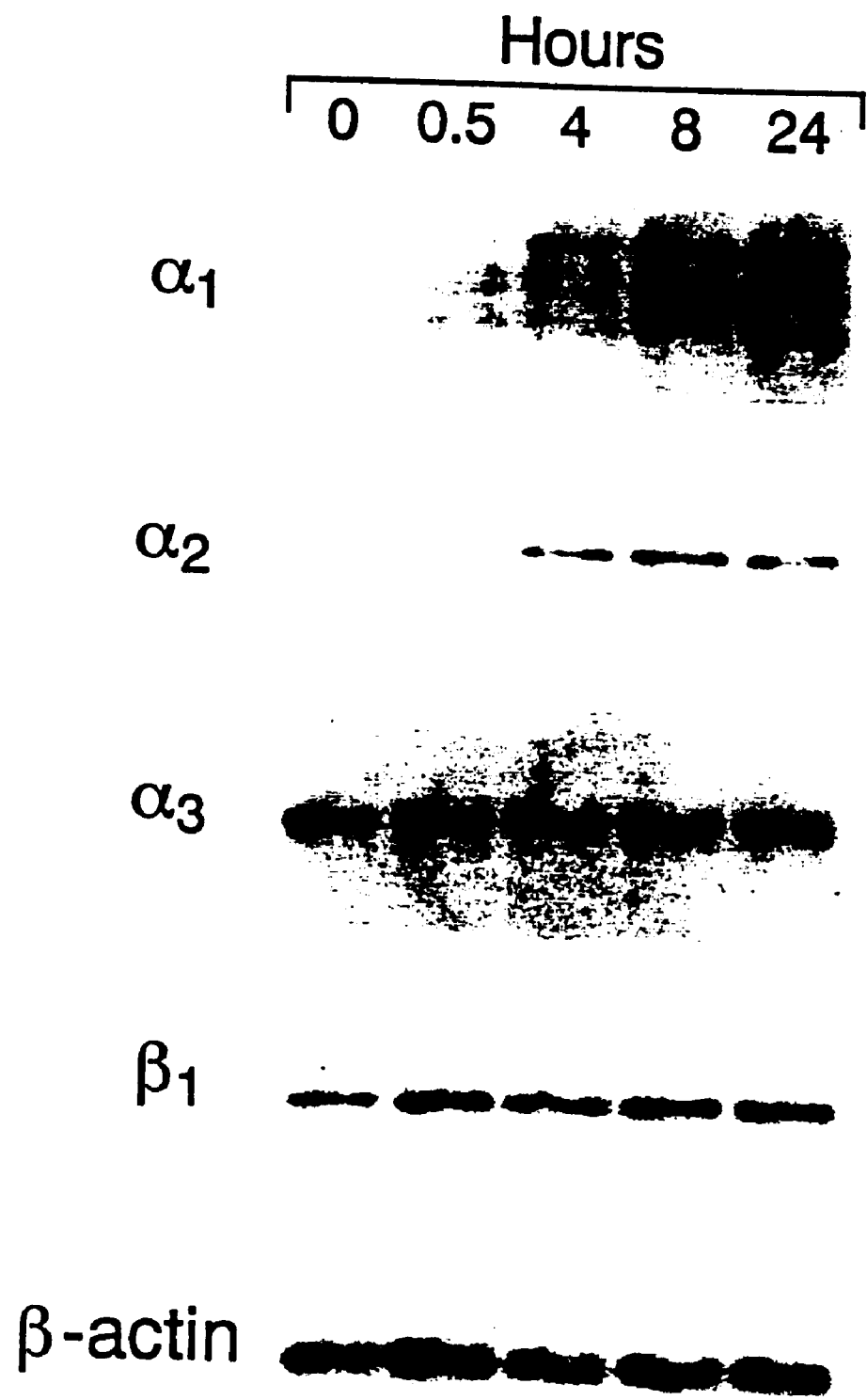
Figure 4B:
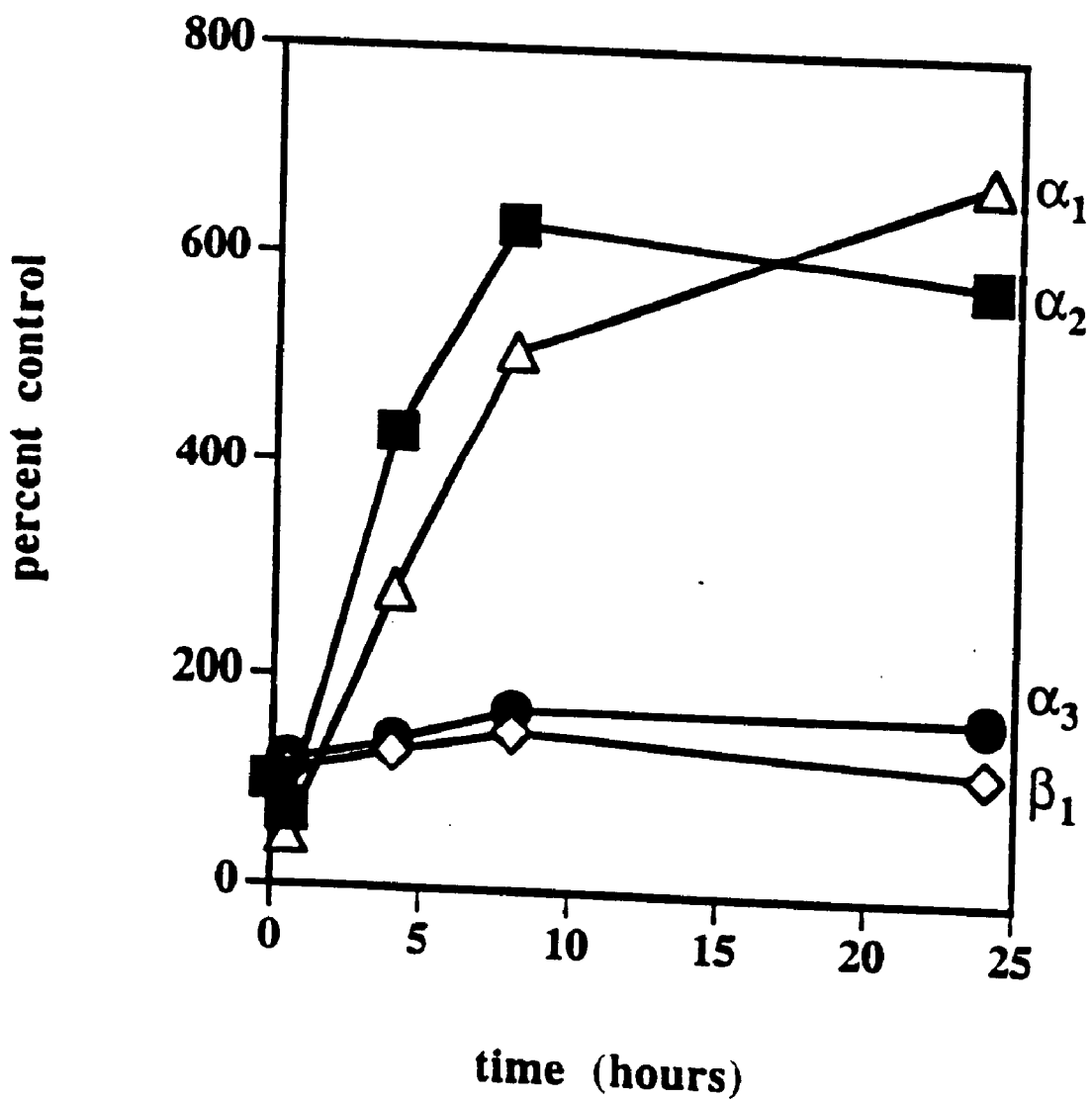
Figure 5:
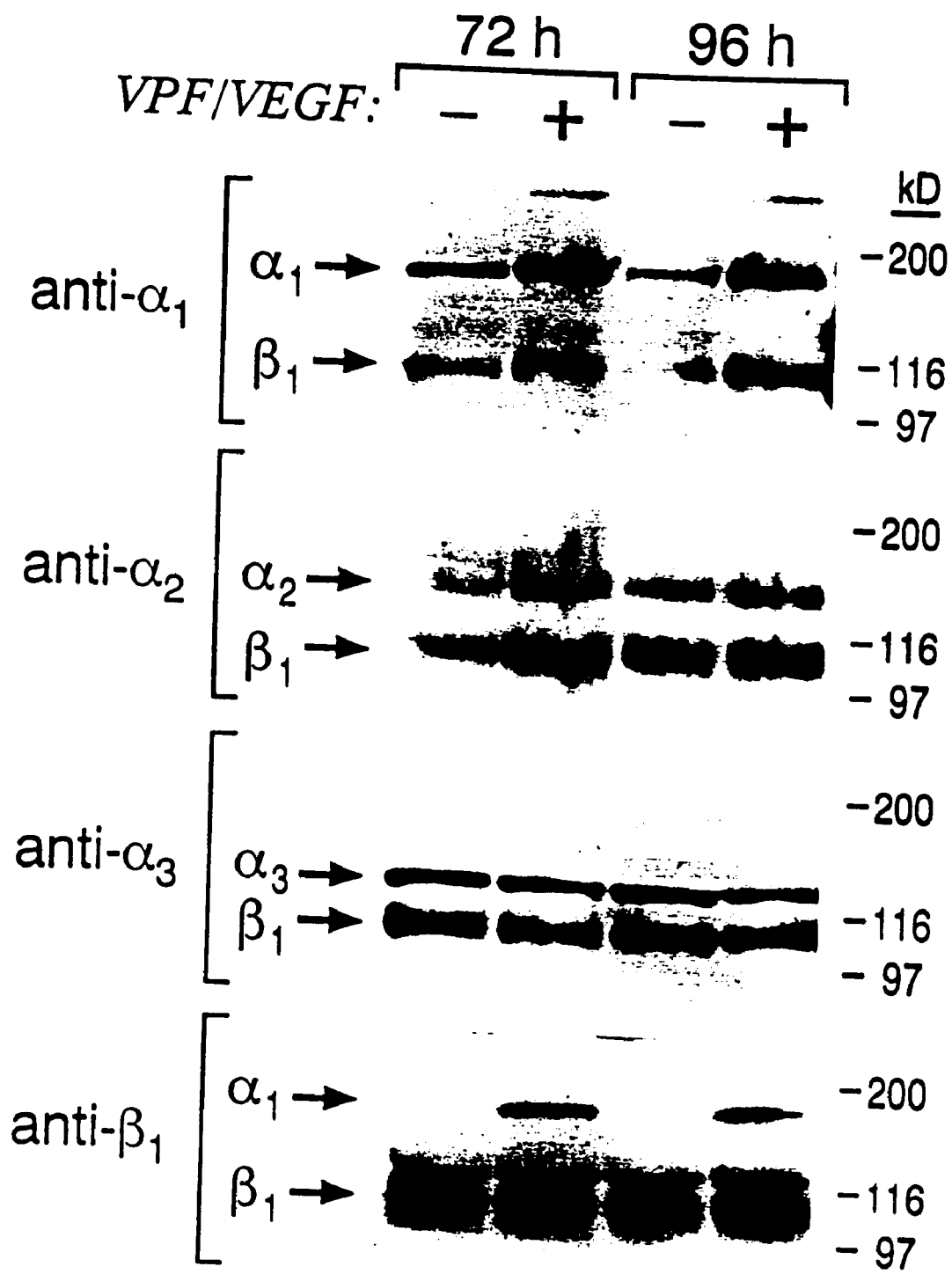
Figure 6D:
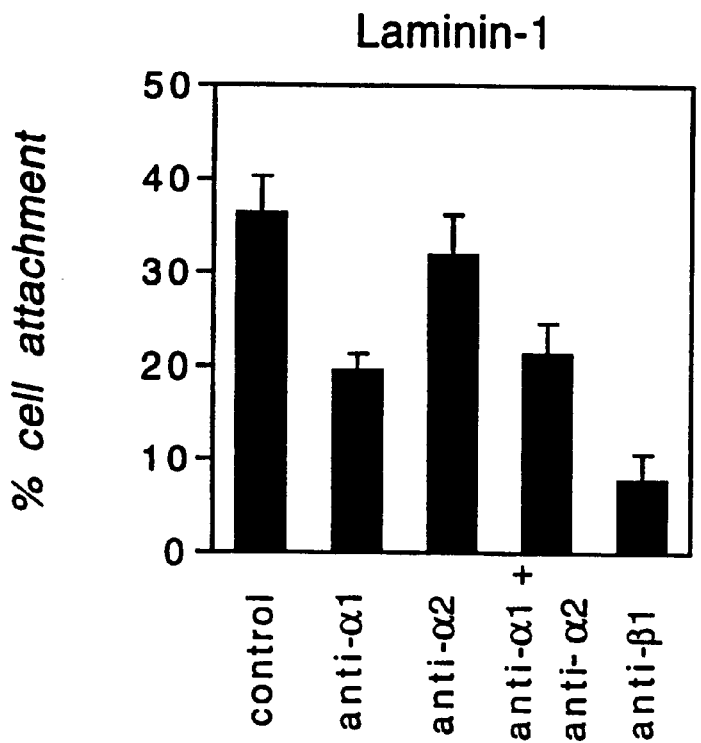
Figure 6E:
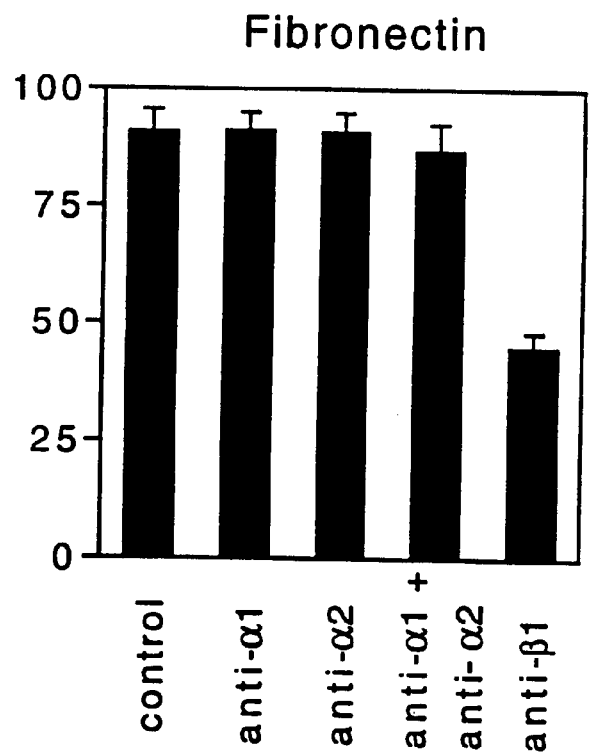

FIG. II is an illustrative correlation showing the presently known possible combinations and permutations between alpha and beta integrin subunits;

FIG. III is an illustrative correlation of the different extracellular matrix ligands able to be bound in-vivo by different combinations of alpha and beta integrin subunits;

FIGS. 1A–B present a statement of the amino acid sequence for the four major variant forms of VEGF;

FIGS. 2A–2C present a statement of the amino acid sequence for the $\alpha_1$ integrin subunit;

FIGS. 3A–3C present a statement of the amino acid sequences for the α2 integrin subunit;

FIGS. 4A and 4B illustrate the qualitative results and densitometric qualities of northern analyses of integrin subunit mRNAs in human dermal endothelial cells stimulated with VEGF for up to 24 hours;

FIG. 5 illustrates integrin expression at the surface of dermal microvascular endothelial cells following stimulation with VEGF for 72 and 96 hours;

FIGS. 6A–6E illustrate the results of ligand-cell cell attachment assays performed with different ligands, dermal microvascular endothelial cells, and specified integrin-blocking monoclonal antibodies;

FIGS. 7A–7D illustrate the spreading of dermal microvascular endothelial cells on type I collagen gels; and FIGS. 8A–8D illustrate the inhibition of VEGF-driven angiogenesis in-vivo by a combination of monoclonal antibodies specific for $\alpha_1$ and $\alpha_2$ integrin subunits.

DETAILED DESCRIPTION OF THE INVENTION

The present invention is a method for inhibiting tumor angiogenesis mediated by vascular endothelial growth factor (VEGF) and specified integrin cell surface receptors induced and expressed in the vasculature of a living subject. As such, this unique inhibition methodology provides both the means and the manipulations for inhibiting new capillary and blood vessel formation effectively and reliably; and also provides multiple advantages and unforeseen benefits both to the physician/clinician as well as for the patient afflicted with a solid tumor mass in-vivo. Some of the uncontemplated advantages and unforeseen benefits include the following:

1. The methodology recognizes for the first time that tumor angiogenesis, mediated in-vivo by vascular endothelial growth factor (VEGF), induces the expression of specified integrin heterodimers, namely $\alpha_1\beta_1$ and $\alpha_1\beta_2$, as cell surface receptors expressed on the endothelial cells lining the vasculature of the subject bearing a solid tumor. The method for inhibiting tumor angiogenesis in-vivo is thus based on this unforeseen recognition of this specific inter-relationship and on a dependence upon VEGF previously secreted by the tumor mass and its in-vivo effect as an inducing agent in order to induce the expression of these specific integrin heterodimers as a requisite forerunner of tumor angiogenesis.

2. The present methodology relies upon and utilizes the novel inducement and expression of specific integrin heterodimers comprised of either the $\alpha_1$ or $\alpha_2$ subunits as the basis and the mechanism of action for inhibiting tumor angiogenesis. The present invention is thus unique in its focus and in its dependence upon the new expression of integrin cell surface receptors constituted of either $\alpha_1$ or $\alpha_2$ subunit moieties as the specific means by which the inhibition can be routinely and reproducibly effected.

3. The present methodology is able to inhibit new capillary and new blood vessel formation both within the tumor mass itself as well as in the immediately adjacent blood vasculature surrounding the perimeter of the tumor mass itself. The method for inhibiting new blood vessel formation is effective for tumor-included blood vessels—those blood vessels and capillaries found within the perimeter edge and substance of the solid tumor mass; and also for tumor-associated blood vessels—those blood vessels lying outside the tumor but within about 0.5 millimeters distance of the tumor mass itself. The present methodology is thus effective and functional in inhibiting both tumor-included and tumor-associated angiogenesis.

4. The present invention has been demonstrated to be effective in inhibiting tumor angiogenesis under in-vivo test conditions. As the experiments and empirical data presented hereinafter clearly evidence and show, the present methodology is effective in inhibiting new blood vessel formation in and around the tumor mass in a reproducible, reliable, and clinically verifiable manner. The present invention is thus deemed to be suitable as a therapeutic technique and clinical tool by which to treat human and animal subjects afflicted with a solid tumor mass in their bodies.

The reader is presumed to be both familiar and acquainted with the published scientific reports and the relevant patent literature regarding VEGF and the integrin molecular family, as well as their functions, their attributes, and their relationship to tumor angiogenesis. However, among this very large body of information known and accumulated to date, it is often difficult, if not impossible, to focus upon unusual features and critical observations which are the foundation of unforeseen developments and unexpected innovations within the field. A summary review of the scientific and evidentiary basis for the present invention will therefore serve the reader and provide the proper factual background and focus for recognizing the truly unique and unforeseen aspects of the present invention.

I. The Tumor Affected by Inhibition of Angiogenesis

It will be recognized and recalled that tumor angiogenesis is the specific development in-vivo of an adequate blood supply for a solid tumor mass. Since the growth of a solid tumor mass in-vivo is believed to be dependent upon the existence, maintenance, and continuing development of a sufficient and functional blood supply and vasculature in-situ, the present invention's goal and objective is to inhibit and prevent the development of the blood supply required by a pre-existing tumor to survive and continue growth. Accordingly, it is the purpose of the present inhibitory methodology to prevent tumor angiogenesis.

With this objective and goal in mind, it is useful to address, identify, and characterize the tumor target which is to be deprived of an adequate blood supply for continued maintenance and growth. For purposes of the present invention, any solid tumor mass lying in any part of the body and in any particular tissue or cell type is suitable as the intended target for inhibition of angiogenesis. It will be recalled that by definition a tumor is a neoplasm—an abnormal mass of cells typically exhibiting uncontrolled and progressive growth. Neoplasms are broadly classified into two categories: (1) according to the cell type from which they originate; and (2) according to their biologic behavior—whether they are benign or malignant. Accordingly, so long as the neoplasm is a solid mass of abnormal cells in which there is a distinct or discrete tumor matrix, stroma, and included and/or associated blood vasculature, that neoplasm is a proper and suitable target for inhibition of tumor angiogenesis using the present methodology.

It will also be recognized that the particular state of the neoplasm or tumor—so long as it is a definable solid mass—does not influence the suitability or use for the present invention. Thus, the tumor may be a "benign" neoplasm—that is, mild, favorable, or kindly (the opposite of malignant). Benign neoplasms are usually well circumscribed and are often encapsulated; and, by definition, do not invade locally and do not metastasize. In comparison, a "malignant" tumor is a neoplasm having the tendency to become clinically progressively worse and to result in the death of the subject. With neoplasms, the term "malignant" denotes the properties of tumor invasiveness and metastasis. In addition, the term "metastasis" is defined as the process by which malignant cells are disseminated from the tumor of origin (the primary tumor) to form a new growth (the secondary tumor) at a distant site; it is the discontinuous extension of a malignant neoplasm. Thus, it is a primary purpose and goal of the present invention to inhibit tumor angiogenesis both in benign and in malignant tumors generally wherever they may be found as a discrete tumor mass.

Accordingly, the present inhibitory methodology is directed to solid tumors found clinically within the living patient in-situ; and the entire broad class of human and animal solid mass tumors is deemed suitable for such therapeutic treatment wherever the tumor may be found within the body. Equally important, and especially for purposes of malignant tumors and neoplasms, the present inhibitory methodology is suitable for use with the tumor regardless of what kind, type, grade, age, size, stage, or cell origin may apply to the tumor in question. Thus, all types of primary and metastatic solid tumors can be treated in-vivo. Representative examples are breast cancer, endometrial cancer, colon cancer, lung cancer, kidney cancer, prostate cancer, glioblastoma of the brain, malignant melanoma, Kaposi's sarcoma, and squamous cell carcinoma of the skin. For these reasons, the present method for inhibiting tumor angiogenesis is deemed to be a broadly applicable and clinically valuable therapeutic treatment.

II. The Underlying Basis for the Present Inhibitory Methodology

The present invention relies on and utilizes three events as working principles. These are:

(1) Mobile vascular endothelial growth factor (VEGF) secreted by the tumor mass in-vivo functions as the initiator molecule only by becoming bound to the surface of an endothelial cell in a tumor-included or a tumor-associated blood vessel. The recognition and functional value of bound VEGF as a requisite mediator and initiator moiety for tumor angiogenesis to occur is now recognized and utilized as a necessary triggering event in-vivo;

(2) The VEGF bound in-vivo on the surface of endothelial cells of tumor-included and tumor-associated blood vessels acts as an unique inducing agent to induce the expression of new specific integrin heterodimers as cell surface receptors on the endothelial cells in-situ; and (3) The newly induced and expressed integrin proteins now serving as cell surface receptors on the endothelial cells of tumor-included and tumor-associated blood vessels are unexpectedly integrin heterodimers comprising the $\alpha_1$ and/or $\alpha_2$ subunits routinely. The inducement, expression, and recognition of the $\alpha_1$ and the $\alpha_2$ subunits in this context has never before been appreciated or utilized for the purpose of inhibiting tumor angiogenesis.

The present invention not only identifies these events as working principles by which tumor angiogenesis proceeds in-situ; but also utilizes these singular findings as the basis of manipulations by which to control and inhibit tumor angiogenesis. The present invention thus recognizes and utilizes in a unique way the fact that VEGF and induced expression of $\alpha_1$ and $\alpha_2$ subunits are uniquely related and involved in a progression of events which culminate as tumor angiogenesis.

The invention recognizes also for the first time that both VEGF and integrin heterodimers comprising the $\alpha_1$ subunit and/or $\alpha_2$ subunits are mediators of tumor angiogenesis; and will be present as part of the phenomenon of tumor angiogenesis as such. Finally, the present invention employs the fact that the newly induced and expressed $\alpha_1\beta_1$ and $\alpha_2\beta_1$ integrin heterodimers present at the surface of endothelial cells of tumor-included and tumor-associated blood vessels can be antagonized using particular antagonistic agents in order to neutralize, block, and deny the functional value of these newly expressed integrin heterodimers as collagen and laminin-1 receptors specifically.

III. The Manipulative Steps Comprising the Present Methodology

The present invention is a methodology which comprises three manipulative steps. Each of the steps comprising the inhibitory treatment reflects and recognizes the underlying principles by which tumor angiogenesis is now understood to proceed; and utilizes these principles; and controls as well as manipulates the progression of events in order to achieve an inhibition of tumor angiogenesis in an effective and reliable manner. Each of the essential manipulative steps will be described individually hereinafter.

Step 1: Allowing Endogenous Mobile VEGF to Become Bound In-Vivo.

First and foremost, the endogenous VEGF which becomes bound in-vivo to the surface receptors of endothelial cells of tumor-included and tumor-associated blood vessels is that tumor-secreted and initially mobile VEGF which subsequently concentrates and binds selectively to the endothelium of tumor-included and/or tumor-associated blood vessels in a far greater degree than is found in normal blood vasculature and normal organs and tissues. By definition, "tumor-included blood vasculature are those blood vessels lying within the tumor stroma and are included within the matrix substance of the solid tumor mass. In comparison, "tumor-associated blood vessels" are those blood vessels lying immediately adjacent to and within about 0.5 millimeters from the solid tumor mass and its microvasculature. Tumor-associated blood vessels include both preexisting and those newly induced by angiogenesis. Both types provide endothelial cells ("EC") which bear surface receptors for VEGF such as Flt-1 and KDR as well as heparin-containing proteoglycans on the cell surface.

VEGF is predominantly synthesized by tumor cells and, generally to a lesser degree, by tumor-associated stromal cells. Thus, the VEGF bound in-vivo on the endothelium cell surface is primarily the result and consequence of previously mobile VEGF that had been synthesized and secreted by the nearby tumor cells.

The entirety of the VEGF which is the inducing agent of the present methodology, is and must be solely that VEGF which becomes bound in-vivo to the endothelial cells of at least one tumor-included or tumor-associated blood vessel. Should freely circulating VEGF be present in any meaningful concentration within the blood of the living subject, such circulating and unbound VEGF is uninvolved and is unrelated to the means of action, the utility, and the purposes of the present invention. It is, therefore, an essential requirement of the present invention that the VEGF in question become bound in-vivo in each and every instance to the surface of the endothelium in a blood vessel lying either within or immediately adjacent to the solid tumor mass itself.

The Requirement

It will be recognized and appreciated that mobile VEGF in fact can be prevented from becoming bound to the surface of endothelial cells in tumor-included and tumor-associated blood vessels in-vivo; and bound VEGF can also be prevented from serving as an inducing agent. The prevention and neutralization of effects in-vivo for mobile VEGF are described by U.S. Pat. Nos. 4,456,550 and 5,036,003. In addition, the in-vivo targeting of bound VEGF function is described by Strawn et al., *Cancer Res.* 56: 3540–3545 (1996).

The present invention, however, does not interrupt and does not prevent the singular cellular consequences stemming from VEGF becoming bound to the surface of endothelial cells in-vivo. To the contrary, it is expressly required that the endogenous VEGF be allowed to bind to the endothelial cells of tumor-included and/or tumor-associated blood vessels; and that such bound VEGF be allowed to act in-situ as an inducing agent in order that new integrin heterodimers be synthesized and expressed at the cell surface of the endothelial cells. This requirement satisfies and is in accordance with the first and second underlying principles as described previously herein.

Structurally and chemically, endogenous VEGF is a dimeric protein which is produced in-vivo in at least four major variant forms as a result of alternative splicing of mRNA [Houck et al., *Mol. Endocrinol.* 5: 1806–1814 (1991); Keck et al., *Science* 246: 1309–1312 (1989); Leung et al., *Science* 246: 1306–1309 (1989); Tischer et al., *Biochem. Biophys. Res. Commun.* 165: 1198–1206 (1989)]. The variants of human VEGF include monomer, single strands of VEGF which are respectively 121, 165, 189, and 206 amino acid residues in length. The precise amino acid sequencing in the primary structure for the four molecular species of VEGF is shown by FIG. 1 (reproduced from Ferrara et al.,

*Endocrine Reviews* 13: 18 (1992)] wherein the identity of each individual amino acid residue in sequence is given by the single-letter code system, as conventionally known and employed routinely in this field.

Figure 1:
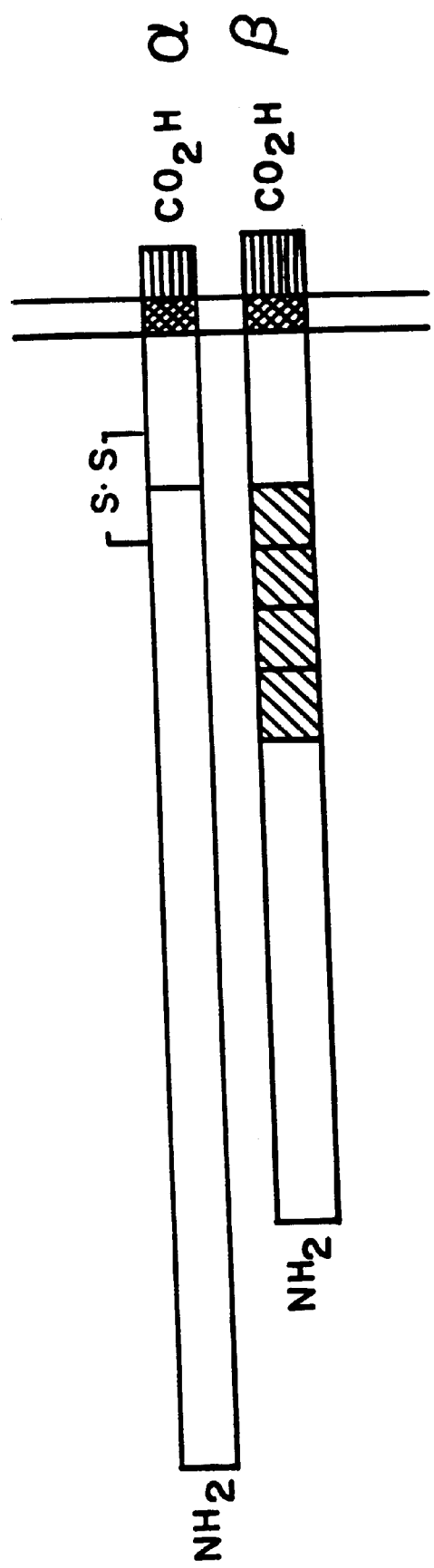

It will be recognized and appreciated from the information of FIG. 1 that the different amino acid segments include omissions in some instances, particularly in the center area of the molecular structure, thereby causing the shorter length strands. In addition, it is noted and recognized that the secreted and released variants of VEGF are generally two of the four: the 121 length variant is secreted and soluble; the 165 length variant is soluble and is the prevalent form which is released. The 189 length variant and the 206 length variant are forms also synthesized and secreted by the tumor cell but are mostly retained by the extracellular matrix of the cell.

Step 2: Allowing the Expression of Integrin Heterodimers Comprising $\alpha_1$ and $\alpha_2$ Subunits It is a requisite of the present methodology that the bound VEGF be permitted to induce the expression of specified integrin heterodimers on the endothelial cell surface of the tumor-included or tumor-associated blood vessel in-vivo. It is also required that the newly induced and expressed integrin heterodimers serving as cell surface receptors be comprised of $\alpha_1$ and/or $\alpha_2$ subunits.

It will be recognized that this step incorporates the underlying second and third principles as described previously herein; and also specifies that the newly induced and expressed integrin heterodimers be composed of either $\alpha_1$ and/or $\alpha_2$ subunits as a requisite result and consequence. It will be appreciated also that the existence of inducable $\alpha_1\beta_1$ and $\alpha_2\beta_1$ integrin heterodimers as a consequence of VEGF activity at the endothelial cell surface is a new finding previously unknown in this field; and also that the induced integrin protein composition must include an alpha subunit selected from the group consisting of $\alpha_1$ and $\alpha_2$ subunits (primarily if not exclusively).

It will also be noted that the specified integrin subunit requirement is exact, precise, and unequivocal. The composition and amino acid sequence of the human $\alpha_1$ subunit is given by FIG. 2 herein, which has been reproduced in part from Briesewitz et al., *J. Biol. Chem.* 268: 2989–2996 (1993). Similarly, the specific amino acid composition and sequence of the human $\alpha_2$ integrin subunit is shown by FIG. 3 herein, which has been reproduced in part from Takada, Y. and M. E. Hemler, *J. Cell Biol.* 109: 397–407 (1989). Moreover, as an aid in recognizing the differing characteristics and properties of the $\alpha_1$ and $\alpha_2$ integrin subunits as discrete compositions of matter, the reader is directed to both of these scientific publications, each of which is expressly incorporated by reference herein.

In addition, as is demonstrated and described experimentally hereinafter, the typical integrin heterodimer induced by VEGF at the endothelial cell surface is the $\alpha_1\beta_1$ protein and the $\alpha_2\beta_1$ protein. As shown by FIG. C herein, both of these expressed integrin heterodimers are specific receptors for collagens or laminin-1 alone. These $\alpha_1\beta_1$ and $\alpha_2\beta_1$ integrin heterodimers are markedly different in their ligand binding specificities and affinities from all other a subunit and g subunit combinations. Equally important, the $\alpha_1$ and $\alpha_2$ integrin subunits do not have a recognition capability for peptides or other kinds of substances carrying the RGD recognition sequence—a trait which is typical of other integrin proteins. For these reasons, the $\alpha_1$ subunit and the $\alpha_2$ subunit are unique and unusual even among the alpha subunit family.

Step 3: Administering at Least One Antagonistic Antibody Preparation Against the Induced and Expressed $\alpha_1$ and $\alpha_2$ Integrin Subunits The third and final manipulation is the administration to the subject of at least one antagonistic preparation effective against the newly induced and expressed specified integrin heterodimers on the endothelial cell surface such that tumor angiogenesis is inhibited in-vivo. For this purpose of explicitly antagonizing the induced and expressed specified integrin units in-situ, the preferred agent is a function-blocking antibody preparation comprised of monoclonal and/or polyclonal antibodies which are specific for epitopes on either or both of the $\alpha_1$ and $\alpha_2$ integrin subunits.

A. The Function-blocking Antibody Antagonist

The preferred function-blocking antibody antagonist will demonstrate two characteristics: It will have the capability of binding specifically to one or more epitopes present within a spatially exposed region of the $\alpha_1$ and/or $\alpha_2$ integrin subunit induced and expressed in vivo. In addition, the other essential characteristic of the specific function-blocking antibody is—that upon binding to the particular alpha integrin subunit, ($\alpha_1$ and/or $\alpha_2$), functional interactions between the integrin heterodimer and its ligands (collagens and laminin-1) will be prevented. Both properties are necessary and required.

The antigenic determinants recognized by the function-blocking antibodies are provided by the amino acid residues comprising the $\alpha_1$ or $\alpha_2$ integrin subunits as shown by FIGS. 2 and 3 respectively herein. However, this specific binding capability can be demonstrated not only by a whole intact antibody, but also by F(ab')$_2$ fragments as well as by Fab fragments derived from the whole antibody structure. It will be recalled that while the whole antibody molecule is a large bulky protein having two specific binding sites, the F(ab')$_2$ fragment represents a divalent binding fragment of the whole antibody; while the Fab binding portion is a univalent binding unit having a minimum of antibody structure. Similar smaller and genetically engineered antibody units having a specific binding capability have also been recently developed; and these entities are deemed to be equally suitable for use herein.

In addition, particular methods for preparing "humanized" antibodies have been devised. See for example, Co, M. S. and C. Queen, *Nature* 351: 501–502 (1919); Winter, G. and W. J. Harris, *TiPs* 14:139–142 (1993); Stephens et al., *Immunology* 85: 668–674 (1995); Kaku et al., *Eur. J. Pharmacol.* 279: 115–121 (1995); and the references cited within each of these publications. Humanized antibodies offer distinct therapeutic advantages; and thus are highly preferred for clinical use because they are less likely to provoke an immune response from the patient undergoing treatment.

Other methods for preparing, isolating, and purifying each of these different antibody binding segments and units are conventionally known in the scientific literature and these techniques have been available for many years as common knowledge in this field. The user may thus chose from among all of these different structured formats—whole antibodies, antibody subunits and antibody fragments—in picking a useful antagonistic structure having a specific binding capability for an epitope in one of the spatially exposed regions of the induced $\alpha_1$ and/or $\alpha_2$ integrin subunits.

In general therefore, the user has the option to chose whether the function-blocking antibody antagonist(s) is obtained from monoclonal, or polyclonal or broad antisera sources. Equally important, the user will decide whether the antibody or antibody fragments should be isolated and purified prior to use; whether they should be altered into humanized antibody form; or whether the antibody antagonist can be employed as a heterogeneous mixture of different entities and varying binding affinities, only some of which will have the requisite affinity and specific binding capability for an exposed epitope on the $\alpha_1$ or $\alpha_2$ integrin subunit expressed in-situ. Thus, the degree of homogeneity, purity, human compatibility, affinity, and specificity of antibodies or antibody fragments and genetically engineered subunits for one or more epitopes of the $\alpha_1$ and $\alpha_2$ integrins is left to the discretion and needs of the user.

Immunogens

The entirety of the $\alpha_1$ and/or $\alpha_2$ integrin subunits or different fragments thereof theoretically can serve as immunogens insofar as antibodies obtained with such immunogens will be evaluated and selected for their specific binding and function-blocking properties.

It will be noted and appreciated also that the range and variety of the intended sites for epitope binding within the induced and expressed $\alpha_1$ and $\alpha_2$ integrin subunits as a whole provides a large number of potential antigenic determinants within each permissible region spatially available for use. Thus, if one choses a peptide fragment as an immunogen, it will be recalled that a minimum of 5–7 amino acid residues (in theory) are able to be employed as a haptene in order to raise specific antibodies within a living host animal. However, longer peptide lengths of at least 10–20 residues are generally preferred. It will be noted also that the various regions in the $\alpha_1$ or $\alpha_2$ integrin structure (shown by FIGS. 2 and 3) available for use as a source of antigenic determinants each provide far longer amino acid residue segments for this purpose. Thus, if an extended segment length of amino acid residues were purposely employed as the immunogen, a larger number of different antigenic determinants becomes available, given the range of residue choices. Accordingly, the number of potential epitopes becomes enormous; yet each of these epitopes is a potential specific binding site for the antibody antagonist(s).

For peptide immunogens, it is intended and envisioned that at least one peptide segment of suitable length (preferably at least 10–20 residues) be chosen as the immunogen in order to provide the antigenic determinants and the production of specific antibodies using a living host animal. Once the amino acid residue length and composition has been chosen (preferably in conformity with the desired requirement of being within a spatially exposed region), the chosen antigenic or haptene segment must be prepared. Often, the desired amino acid segment can be synthetically prepared using conventionally known solid phase peptide synthesis methods [such as Merrifield, R B, *J. Am. Chem. Soc.* 85: 2149 (1963)]. Once synthesized, it is most desirable that the chosen segment be purified (such as by gel filtration) and desirably analyzed for content and purity (such as by sequence analysis and/or mass spectroscopy).

After its isolation or synthesis, the chosen peptide segment is typically coupled to a protein carrier to form the immunogen. Conventionally suitable protein carriers available for this purpose are available in great variety from many diverse sources. The only requirements regarding the characteristics and properties of the carrier are: first, that the protein carrier be in fact antigenic alone or in combination with the synthesized chosen amino acid residue sequence; and second, that the carrier protein be able to present the antigenic determinants of the residue sequence such that antibodies specific against the amino acid residues are produced in a living host animal. Clearly, as the experiments described hereinafter, the preferred choice of protein carrier for immunization purposes include keyhold limpet hemocyanin (KLH), coupled by glutaraldehyde (GLDH), sulfo-m-maleimidobenzo (M-hydroxysuccinimide) ester (MBS), or bisdiazobenzidine (BDB). However, any other carrier protein compatible with the host to be immunized is also suitable for use. Example of such other carrier proteins include bovine serum albumin, thyroglobulin, and the like.

Immunization Procedure

All immunizations and immunization procedures are performed in the conventionally known manner described in the scientific literature. It is expected that under certain use conditions, adjuvants will be employed in combination with the prepared immunogens. Alternatively, the prepared immunogens may be used alone and be administered to the animal or human host in any manner which will initiate the production of specific antibodies.

In addition, the harvesting of polyclonal antiserum and the isolation of antibody containing sera or antibody producing cells follows the conventionally known techniques and processes for this purpose. Similarly, the preparation of hybridomas follows the best practices developed over recent years for the isolation of monoclonal antibodies [Marshak-Rothstein et al., *J. Immunol.* 122: 2491 (1979)].

Polyclonal and Monoclonal Antibodies

Once obtained, the polyclonal antisera and/or monoclonal antibodies and/or genetically engineered antibodies should be evaluated and verified for their ability to bind specifically with an epitope existing within a spatially exposed region the $\alpha_1$ or $\alpha_2$ integrin subunits and for the capability to functionally block the abilities of the $\alpha_1\beta_1$ and $\alpha_2\beta_1$ heterodimers to bind to collagens and laminin-1. If desired, cleavage with papain will produce two Fab fragments plus the Fc fragment; whereas cleavage of the antibodies with pepsin produces the divalent F(ab')$_2$ fragment and the Fc' fragment—all as conventionally known.

It will be expressly understood, however, that regardless of whether the antibody binding portion represents polyclonal antisera, monoclonal antibodies, the F(ab')$_2$ fragment, Fab fragments, humanized antibodies, or other antibody species—all of these are suitable and intended for use so long as the specific function blocking capability is demonstrated after binding to at least one epitope existing within the $\alpha_1$ and/or $\alpha_2$ integrin subunits induced and expressed in-vivo. It is therefore deemed to be expected that a wide variety of different immunoassay systems will be employed to demonstrate the specific binding and function-blocking capabilities required by the antibody antagonists of the present invention; and that the parameters of concentration, volume, temperature, carriers, and delivery systems can be varied extensively at will when choosing antibodies and/or antibody fragments and subunits. The present invention therefore presumes and incorporates by reference any conventionally known immunoassay technique, procedure, protocol, or other factor or parameter—all of which may be usefully employed for the evaluation and/or preparation of a specifically binding and functionally-blocking antibody antagonist.

Conventionally Obtainable Examples

A number of antagonistic monoclonal antibody preparations have already been reported in the scientific literature or are now commercially sold which are specific binding and function-blocking antagonists of the $\alpha_1$ or $\alpha_2$ integrin subunits. Representative of such antagonistic monoclonal antibodies reported in the scientific literature are those listed within Table 2 below. In addition, representative examples of commercially prepared anti-$\alpha_1$ and anti-$\alpha_2$ integrin specific and function-blocking monoclonal antibodies (MAbs) are those sold by PharMingen Corp. as described within Table 3 below. Lastly, representative examples of specifically binding and functionally-blocking mouse monoclonal antibodies (raised against purified human $\alpha_1$ or human $\alpha_2$ integrin proteins) which are commercially sold by Upstate Biotechnology Corp. are listed within Table 4 below.

TABLE 2

Conventional Function-Blocking Monoclonal Antibodies Specific for $\alpha_1$ or $\alpha_2$ Integrin Subunits

| Name of MAb | Integrin Target | Published Reference |
|---|---|---|
| P1H5 | $\alpha_2$ subunit | Staatz etal., J.CellBiol.108: 1971–1924 (1989); Staatz etal., J.Biol.Chem.265:4778–4781 (1990) |
| FB12 | $\alpha_1$ subunit | Fabbri etal., TissueAntigens48: 47–51 (1996) |
| 5E8D9 | $\alpha_1$ subunit | Lugue etal., FEBSLetters346: 278–284 (1994) |

TABLE 3*

A. Purified Hamster Anti-Rat/Mouse CD49a (Integrin $\alpha_1$ chain), Function-Blocking, Monoclonal Antibody (No Azide/Low Endotoxin)

Product Information

| | |
|---|---|
| Catalog Number | 22620S, 2.0 mg. |
| Description: | Purified hamster anti-rat/mouse CD49a (Integrin $\alpha_1$ chain) |
| Clone: | Ha31/8 |
| Isotope: | Armenian Hamster IgG |
| Contents: | Purified immunoglobulin in 10 mM phosphate buffer, pH 7.2 with 150 mM NaCl (0.2 µm filtered). No sodium azide. Endotoxin level is ≦0.01 ng/µg of protein. |

Specificity

The Ha31/8 antibody reacts with the 180-kDa integrin $\alpha_1$ chain (CD49a), which is a transmembrane glycoprotein that non-covalently associates with the integrin $\beta_1$ (CD49a/CD29 or VLa-1) complex. VLA-1 is expressed on activated T cells, smooth muscle cells, and endothelial cells; and it is a receptor for collagen and laminin.[1] The immunogen for the Ha31/8 clone was emulsified rat glomeruli, and the monoclonal antibody is specific for both rat and mouse CD49a.[2,3] It has been reported that Ha31/8 antibody can block VLA-1-mediated binding to collagen.[3]

References

1. Miyake, S., T. Sakurai, K. Okumura, and H. Yagita. "Identification of collagen and laminum receptor integrins on murine T lymphocytes". Eur. J. Immunol. 24: 2000–2005 (1994).
2. PharMingen. Unpublished data.
3. Mendrick, D. L., D. M. Kelly, S. S. DuMont, and D. J. Sandstrom, "Glomerular epithelial and mesangial cells differentially modulate the binding specificities of VLA-1 and VLA-2", Lab. Invest. 72: 367–375 (1995).

B. Purified Hamster Anti-Mouse CD49b (Integrin α2 chain), Function-Blocking, Monoclonal Antibody (No Azide/Low Endotoxin)

Product Information

| | |
|---|---|
| Catalog Number: | 09790S, 3.0 mg |
| Description: | Purified anti-mouse CD49b (Integrin $\alpha_2$ chain) |
| Clone: | HMα2 |
| Isotype: | Armenian Hamster IgG |
| Contents: | Purified immunoglobin in 10 mM phosphate buffer, pH 7.2 with 150 mM NaCl (0.2 µm filtered). No sodium azide. Endotoxin level is ≦0.01 ng/µg of protein. |

Specificity

The HM$\alpha_2$ antibody recognizes integrin $\alpha_2$ chain (CD49b), the 150-kDa transmembrane glycoprotein that non-covalently associates with the integrin $\beta_1$ subunit (Cd29) to form the integrin $\alpha_2\beta_1$ complex known as VLA-2, which is a receptor for collagen and laminin.[1] VLA-2 is expressed on some splenic CD4+T lymphocytes,[1,2] on intestinal intraepithelial and lamina propria lymphocytes,[3] NK cells,[2] and platelets,[2] but it is not on thymocytes[1] nor Peyers patch, peripheral lymph nodes and mesenteric lymph nodes lymphocytes.[3] The expression of VLA-2 is upregulated on lymphocytes in response to motigens.[1] The HM$\alpha_2$ antibody has been reported to partially block the interaction of T-cell blasts with collagen.[1,4]

TABLE 3*-continued

References

1. Miyake, S., T. Sakurai, K. Okumura and H. Yagita. Identification of collagen and laminin receptor integrins on murine T lymphocytes, Eur. J. Immunol. 24: 2000–2005 (1994).
2. PharMingen. Unpublished results.
3. Tanaka, T., Y. Ohtsuka, H. Yagita, Y. Shiratori, M. Omata, and K. Okumura, Involvement of $\alpha_1$ and $\alpha_4$ integrins in gut mucosal injury of graft-versus-host disease. Int. Immunol. 7: 1183–1189 (1995).
4. Noto, K., K. Kato, K. Okumura and H. Yagita, "Identification and functional characterization of mouse CD29 with a mAb," Int. Immunol. 7: 835–842 (1995).

*Source: PharMingen Corp., San Diego, CA; Technical Data Sheets.

TABLE 4*

A. Anti-Human Integrin $\alpha 1$ (CD49a, VLA$\alpha 1$), Function-Blocking, Mouse Monoclonal IgG

| | |
|---|---|
| Antibody Class: | IgG$_{2a}$, purified by protein A affinity chromatography. |
| Immunogen: | Purified human Integrin $\alpha 1$. |
| Source: | From hybridoma produced by fusing SP2/0 mouse myeloma cells with immunized Balb/c splenocytes, and propagated as mouse ascites. |
| Clone 5E8D9. | |
| Formulation: | Frozen liquid. |
| Quantity: | 200 μg/vial in 116 μl 0.1M Tris-glycine, pH 7.4, containing 0.05% sodium azide. |
| Specificity: | |

Integrin $\alpha 1$.
Species cross-reactivity not determined.
References

1. Luque et al., FEBS Letter 346: 278–284 (1994).
2. Arroyo et al., J. Cell Biol. 117: 659–670 (1992).

B. Anti-Human Integrin $\alpha 2$ (CD49b, VLA-2), Function-Blocking, Mouse Monoclonal IgG.

| | |
|---|---|
| Immunogen: | A549 human lung carcinoma cell line. |
| Antibody Class: | IgG, purified by protein G affinity chromatography. |
| Source: | From hybridoma produced by fusing P3XAg8.653 mouse myeloma cells with immunized RBF/DnJ splenocytes, and propagated as mouse ascites. |
| Clone A2-IIE10. | |
| Species Cross-reactivity: | The A2-IIE10 antibody does not recognize mouse $\alpha 2$. Other non-human species have not been tested. |
| Quantity: | 200 μg/vial in 75 μl 0.1M Tris-glycine, pH 7.4, containing 0.05% sodium azide. |
| Physical Form: | Frozen solution. |
| References | |

Lee et al., Cir. Res. 76: 209–214 (1995).
Bergelson et al., Cell Adh. & Comm. 2: 455 (1994).

*Source: Upstate Biotechnology Corp., Lake Placid, NY; Certificates of Analysis.

IV. The In-Vivo Inhibition of Tumor Angiogenesis and its Therapeutic Treatment Potential The consequence in-vivo of practicing the present methodology properly and completely in all its manipulative steps will provide and produce an effective inhibition of tumor angiogenesis as a clinically recognizable consequence and benefit. The present invention will provide a reliable and useful procedure for denying an adequate blood supply to solid tumors in-vivo within the body of a human or animal subject. The clinical effectiveness of the inhibition methodology has been demonstrated not only by in-vitro experiments but also unequivocally shown by the empirical data provided by in-vivo animal subjects.

Dosages, Modes of Administration, and Pharmaceutical Formulations

Compositions embodying the specifically binding and functionally-blocking antagonistic antibody for the present invention can be administered in any manner which preserves the function of the antibody and delivers it to the tumor site—such as intravenous, subcutaneous or other parenteral administration. The prepared antagonistic antibody can be introduced by any means or routing that inhibits tumor angiogenesis as described.

The dosage to be administered to any patient will vary and be dependent upon the age, overall health, and weight of the human or animal recipient; the kind of concurrent treatment, if any; the frequency of concurrent treatment; and the physician's prognosis for the patient. Generally, a range doses of antagonistic antibody from 0.1 milligrams to about 10.0 milligrams per kilogram of body weight, in twice weekly or three times weekly administrations is expected to be effective to yield the desired therapeutic result.

The duration of antagonistic antibody dose administration is expected to be continued so long as a favorable clinical result is obtained. It is believed that this treatment regimen will inhibit tumor angiogenesis in-vivo; and, in this manner, act to retard or halt the growth of the solid tumor in-situ. However, it is as yet unclear whether or not this inhibitory treatment method will provide for complete regression of tumor. For this reason especially, the treatment duration and dosage should be monitored accordingly.

In addition, since the antagonistic antibody preparation is typically to be given intravenously, subcutaneously, or other parenteral applications, the appropriate quantity of antibody will be prepared in sterile form; exist in single or multiple dose formats; and typically be dispersed in a fluid carrier such as sterile physiological saline or 5% dextrose solutions commonly used with injectables.

V. Experimental and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Materials and Methods
Cells, Cell Culture, and VEGF Stimulation

Human dermal microvascular endothelial cells (hereinafter "EC") were isolated from neonatal foreskins as described previously [Detmar et al., *J. Invest. Dermatol.* 39: 2195–2225 (1990)]. Cells were grown on collagen-coated dishes in a fully supplemental endothelial cell basal medium (Clonetics, San Diego, Calif.) containing 20% fetal calf serum (Gibco BRL, Grand Island, N.Y.), 50 $\mu$M dibutyryl cyclic AMP, 1 $\mu$g/ml hydrocortisone acetate, 100 U/ml penicillin, 100 U/ml streptomycin, and 250 $\mu$g/ml amphotericin B (Sigma Chemical Co., St. Louis, Mo.).

Endothelial cells at passage 4 to 7 were seeded at a concentration of $1\times10^4$ cells/cm$^2$ into 100 mm plastic dishes (Costar, Cambridge, Mass.) in fully supplemented growth medium (see above). Media were replaced every second day until the cells were confluent. For those experiments involving Northern analysis, confluent cells were shifted to EC basal medium supplemented only with 2% fetal calf serum and antibiotics 24 h prior to stimulation with VEGF. For those experiments involving stimulation with VEGF for 72 h or longer, confluent cells were shifted to this medium when VEGF was added. Recombinant human VEGF$_{165}$, which is the principal VEGF isoform, was purchased from R&D Systems (Minneapolis, Minn.) and was added to EC cultures as indicated in the experimental descriptions. All experiments were performed at least twice with similar results.

RNA Isolation and Northern Analyses

Total cellular RNA from EC was isolated, subjected to electrophoresis, and transferred to nylon membranes as previously described [Senger et al., *Am. J. Path.* 149: 293–305 (1996)]. $^{32}$P-labeled cDNA probes were prepared as described therein using purified cDNA inserts isolated from the following: human $\alpha_2$ integrin plasmid (clone 2.72F) and human $\alpha_3$ integrin plasmid (clone 3.10) from the American Type Culture Collection (Rockville, Md.); human $\alpha$1 integrin plasmid (clone 3RA), generously provided by Dr. Eugene Marcantonio (Columbia U., New York, N.Y.); and a plasmid containing a 2.5 kb human $\beta_1$ cDNA insert, generously provided by Dr. Larry Fitzgerald (U. Utah, Salt Lake City, Utah). A purified 2.0 kb human $\beta$-actin cDNA was purchased from Clontech (Palo Alto, Calif.). Hybridizations were performed as described in Kaye et al. [*Proc. Natl. Acad. Sci. USA* 89: 8542–8546 (1992)]; and autoradiograms were subjected to quantitation with a Gel Doc 1000 Imaging Densitometer (Bio-Rad Laboratories, Richmond, Calif.).

Cell Surface Biotinylation and Immunoprecipitation Analyses

Surface labeling with biotin was performed essentially as described in Shaw et al. [*J. Biol. Chem.* 268: 11401–11408 (1993)] except that the endothelial cells were suspended at a final concentration of $2\times10^6$ cells/ml and NHS-LC-biotin (Pierce Chemical Co., Rockford, Ill.) was dissolved in phosphate buffered saline (PBS) and added to the cells at a final concentration of 1 mM. The biotin labeling reaction was allowed to proceed for 30 min. at room temperature with gentle agitation to maintain the cells in suspension. Then, after washing the cells twice in PBS with 50 mM ammonium chloride to eliminate and quench the biotinylating reagent, the endothelial cells were lysed in detergent-containing immunoprecipitation buffer as described previously [Senger et al., *Am. J. Path.* 149: 293–305 (1996)]. Following extraction for 30 min. at 4° C., 1.0 ml lysates were centrifuged (29,000×g) at 4° C. for 30 min. To control for differences in cell recovery and/or biotinylation efficiency, equal volumes of lysates were subjected to polyacrylamide gel electrophoresis and transferred to PVDF membrane (Millipore Corp., Bedford, Mass.). Total biotinylated protein was then visualized with chemiluminescence as described in Shaw et al. [*J. Biol. Chem.* 268: 11401–11408 (1993)]. Images were captured on x-ray film and quantitated with imaging densitometry. The differences, if any, were minor; and lysate volumes were normalized accordingly for immunoprecipitation.

Immunoprecipitation was performed as described previously [Senger et al., *Am. J. Path.* 149: 293–305 (1996)]. Specific rabbit polyclonal antisera (Abs) to $\alpha_1$ integrin, $\alpha_2$ integrin, and $\alpha_3$ integrin subunits were purchased from Chemicon International (Temecula, Calif.). Rabbit polyclonal Ab to the $\beta_1$ subunit was generously provided by Dr. Richard Hynes (MIT, Cambridge, Mass.). All of these polyclonal Abs were raised against synthetic peptides representing C-terminal sequences of the respective integrin subunits. Immunoprecipitates were subjected to electrophoresis; transferred to PVDF membrane; visualized with chemiluminescence; and protein bands were quantitated as described above. Biotinylated protein standards purchased from Bio-Rad included myosin (Mr 200,000), $\beta$-galactosidase (Mr 116,000) and phosphorylase B (Mr 97,400).

Cell Attachment and Cell Spreading Assays

For cell attachment assays, 96 well plates (Corning Costar Corp., Cambridge, Mass.) were coated with matrix proteins at a concentration of 10 $\mu$g/ml for 1 hr followed by a coating of 100 mg/ml bovine serum albumin (Cat. #A9306, Sigma Chemical Co., St. Louis, Mo.) for 2 h to block the remaining protein binding sites. The coating of matrix proteins included human placental collagen I and mouse EHS laminin-1 (Life Technologies, Grand Island, N.Y.) and human placental collagens IV and V (Collaborative Biomedical, Bedford, Mass.). Cultured cells were prelabeled with fluorescent Cell Tracker Dye (Molecular Probes, Eugene, Oreg.) at a concentration of 3 $\mu$M for 30 min. and then incubated with fresh medium for 60 min. to remove any unincorporated dye. Labeled cells were gently trypsinized and suspended in serum-free medium at $1.5\times10^5$ cells/ml, mixed with antibody (see below) as indicated for 15 minutes. 100 $\mu$l of prepared cell suspension was then added to each well. After the expiration of 45 min., the unattached cells were removed by washing; and the attached cells were quantitated with a fluorescence plate reader. Attachment of the cells to the wells coated with BSA alone were negligible. Control mouse IgG and mouse monoclonal blocking antibody specific for the human $\beta_1$ integrin subunit (clone P4C10) were purified from control serum and P4C10 ascites (Life Technologies), respectively, using the MAPS II antibody purification kit (Bio-Rad). Purified mouse monoclonal blocking antibodies specific for the human $\alpha_1$ integrin subunit (clone 5E8D9) and specific for the $\alpha_2$ integrin subunit (clone A2-IIE10) were purchased from Upstate Biotechnology (Lake Placid, N.Y.).

To assess cell spreading on collagen I gels, Vitrogen (bovine dermal collagen I, Collagen Corp., Palo Alto, Calif.) was neutralized according to the manufacturer's instructions; diluted to a final concentration of 500 µg/ml with serum-free medium; and then added to 24 well plates (500 µl/well). After the diluted Vitrogen had polymerized at 37° C., $1.2 \times 10^5$ cells were added to each well containing antibodies (see above).

Mouse Angiogenesis Assays and Analyses of Angiogenesis Inhibition by Integrin Specific Antibodies The assay employed was essentially as described previously by Passaniti et al. [*Lab. Invest.* 67: 519–528 (1992)] with the following modifications. Athymic NCr nude mice (7–8 weeks old, females) were injected subcutaneously midway on the right and left back sides with 0.25 ml Matrigel (Collaborative Biomedical, Bedford, Mass.) at a final concentration of 10 mg/ml together with $2.5 \times 10^6$ VEGF-transfected SK-MEL-2 cells [Claffey et al., *Cancer Res.* 56: 172–181 (1996)]. Soon after injection, the Matrigel implant solidified and persisted without apparent deterioration throughout the six day assay interval. The animals were individually treated with one of the following purified, low endotoxin ($\leq 0.01$ ng/µg protein), hamster monoclonal antibodies ("MAbs", Pharmingen, San Diego, Calif.): $\alpha_1$-blocking MAb (clone Ha31/8); $\alpha_2$-blocking MAb (clone HA$\alpha_2$); or control isotype standard anti-TNP MAb (clone G235–2356). After six days, the treated animals were individually euthanized and dissected; and the excised implants were then photographed.

The excised implants together with associated skin were fixed for 60 min. in 10% formalin and embedded in paraffin. Histological sections were cut, deparaffinized, and treated with 0.1% trypsin for 30 min. at 37° C. to enhance antigen availability to CD31 rat monoclonal antibody (clone MEC13.3, Pharmingen). Bound rabbit (anti-rat) secondary antibody, coupled to horseradish peroxidase (Vector Labs, Burlingame, Calif.), was visualized with True Blue peroxidase substrate (Kirkegaard and Perry Labs, Gaithersburg, Md.). The sections were counterstained with nuclear fast red (Vector Labs). Cross-sectional diameters of new blood vessels at the implant/host interface were measured from representative photographs; and the resulting data was expressed as average diameter size±standard deviation (n=60 for both groups). To determine statistical significance, the empirical data were subjected to the unpaired t test.

Experimental Series I: VEGF induction of $\alpha_1\beta_1$ and $\alpha_2\beta_1$ Expression by Human Dermal Microvascular EC Experiment A Endothelial cells were stimulated with VEGF165 (20 ng/ml) for up to 24 h; and mRNAs endocing $\alpha_1$, $\alpha_2$, $\alpha_3$, and $\beta_1$ integrin subunits were quantitated by Northern analysis. Unstimulated cells, cultured in parallel, served as controls. The results are shown by FIGS. 4A and 4B.

FIG. 4A shows the results of Northern analysis of integrin subunit mRNAs in human dermal microvascular EC stimulated with VEGF (20 ng/ml) for up to 24 h. Ten micrograms of local cellular RNA was loaded in each well. In comparison, FIG. 4B shows the densitometric quantitation of the Northern analyses. The signal associated with each integrin mRNA was normalized to the internal β-actin mRNA standard to adjust for minor differences in RNA loading.

As shown by FIG. 4, VEGF stimulation resulted in a >6-fold induction of $\alpha_1$ and $\alpha_2$ mRNAs. In contrast, VEGF-stimulated cells showed no induction of $\alpha_3$ mRNA or $\beta_1$ mRNA, in comparison with unstimulated cells. In addition, $\alpha_5$ mRNA was not induced by VEGF stimulation (data not shown).

Experiment B

To determine if inducation of $\alpha_1$ and $\alpha_2$ mRNAs by VEGF translated to increased expression of $\alpha_1\beta_1$ and $\alpha_2\beta_1$ heterodimers at the EC surface, the cells were stimulated with VEGF for 72 h or 96 h; the cell surface proteins were labeled covalently with NHS-LC-biotin; and immunoprecipitations were performed with relevant antibodies. Equal numbers of control and stimulated cells were subjected to surface biotinylation; and minor differences in cell recovery and biotinylation were controlled for quantitating incorporated biotin (see Materials and Methods). The results are illustrated by FIG. 5.

FIG. 5 shows integrin expression at the surface of dermal microvascular EC following stimulation with VEGF (20 ng/ml) for 72 h and 96 h. Lysates from biotinylated cells were subjected to immunoprecipitation; and the immunoprecipitates were then subjected to electrophoresis in 7.5% polyacrylamide gels under non-reducing conditions. Control cells were cultured and biotinylated in parallel. As determined by densitometry, $\alpha_1\beta_1$ and $\alpha_2\beta_1$ expression typically were induced 5- to 7-fold by the VEGF treatment.

Accordingly, as shown in FIG. 5, stimulation of EC with VEGF resulted in a markedly increased expression of $\alpha_1\beta_1$ and $\alpha_2\beta_1$ at the cell surface. The induction and expression of $\alpha_1\beta_1$ and $\alpha_2\beta_1$ integrin units were confirmed in multiple experiments (>5); and densitometric quantitation indicated 5- to 7-fold induction for both the $\alpha_1\beta_1$ and $\alpha_2\beta_1$ integrins. In contrast, expression of the $\alpha_3\beta_1$ integrin was not induced by VEGF stimulation.

Experimental Series II: EC Attachment Mediated By $\alpha_1\beta_1$ and $\alpha_2\beta_1$ Integrins The $\alpha_1\beta_1$ and $\alpha_2\beta_1$ integrins are known to bind collagens and laminin-1; and $\alpha_2\beta_1$ also has been reported to bind tenascin. However, the ligand binding specificities of these integrins are not absolute and are known to differ among cell types. Therefore, these experiments tested the attachment of 72 h VEGF-stimulated microvascular EC to collagens I, IV, and V, and to laminin-1 in the presence of $\alpha_1$-blocking MAb and/or $\alpha_2$-blocking MAb in comparison with β-blocking. MAb and control IgG. The results are illustrated by FIGS. 6A–6E respectively.

FIGS. 6A–6E show the results of ligand to cell attachment assays performed with dermal microvascular EC and integrin-blocking MAbs. Cultured cells were stimulated with VEGF (20 ng/ml, 72 h) prior to assay for maximal induction and expression of $\alpha_1\beta_1$ and $\alpha_2\beta_1$ integrin units. Substrata were coated with matrix proteins, followed by a coating of BSA to block the remaining protein binding sites. Cells were allowed to attach for 45 minutes time in serum-free medium; control IgG and specific MAbs were employed at a concentration of 10 μg/ml.

As shown by FIG. 6, the $\alpha_1$ MAb and $\alpha_2$ MAb each partially blocked cell attachment to collagen I; and the two MAbs in combination together inhibited cell attachment at >90% of cell instances. The $\beta_1$ MAb similarly inhibited cell attachment at >95% values. Although $\alpha_1$ MAb and $\beta_1$ MAb inhibited cell attachment of VEGF-stimulated cells to collagen IV, cell attachment was not inhibited by $\alpha_2$ MAb. Also only relatively poor attachment of VEGF-stimulated cells to collagen V was observed—an event which was inhibited most significantly by $\alpha_1$ MAb or $\beta_1$ MAb. Moreover, adhesion to laminin-1 was blocked by $\alpha_1$ MAb and $\beta_1$ MAb but little or no inhibition of cell attachment was found with the $\alpha_2$ MAb. Finally, no inhibition of cell attachment to fibronectin was observed using either $\alpha_1$ MAb or $\alpha_2$ MAb. Thus, these experiments demonstrate that the $\alpha_1\beta_1$ and $\alpha_2\beta_1$ integrins present on the surface of VEGF-stimulated microvascular EC each were important for mediating cell attachment to collagen I; and that the $\alpha_1\beta_1$ integrin also mediated EC attachment to collagens IV and V, and laminin-1.

Experimental Series III: VEGF-Induced Expression of $\alpha_1\beta_1$ and $\alpha_2\beta_1$; Consequences for EC Interactions with Three-Dimensional Collagen Gels In-Vitro Interactions between microvascular EC and three-dimensional collagen gels (i.e., polymeric collagen) are deemed to be more relevant to angiogenesis than interactions between cells and collagen-coated plastic (i.e., planar collagen). Therefore, the consequences of increased $\alpha_1\beta_1$ and $\alpha_2\beta_1$ integrin unit expression for interactions between microvascular EC and polymeric collagen was investigated. For these experiments, the unstimulated control and 72 h VEGF prestimulated EC were plated on type I collagen gels in the presence of control or integrin-blocking MAbs. The results are illustrated by FIGS. 7A–7D respectively.

FIGS. 7A–7D show the spreading of dermal microvascular EC on type I collage gels. The control comprised unstimulated cells which were cultured in parallel with EC prestimulated with VEGF (20 ng/ml) for 72 h. Control and VEGF prestimulated cells were plated with serum-free medium on collagen gels in the absence of VEGF. After 4 h, cells were photographed. A combination of $\alpha_1$-blocking MAb and $\alpha_2$-blocking MAb (10 μg/ml of each) abolished cell spreading of the VEGF prestimulated cells; the control IgG (20 μg/ml) was observed to be without effect.

As shown in FIG. 7, 72 h VEGF prestimulation promoted EC spreading on polymeric collagen as compared to unstimulated EC. Similar results were obtained with EC embedded in type I collagen (data not shown). Clearly, the addition of $\alpha_1$-blocking MAb in combination with $\alpha_2$-blocking MAb completely inhibited spreading of the VEGF-stimulated cells. Individually, the $\alpha_1$ MAb and $\alpha_2$ MAb each partially inhibited cell spreading—indicating that both $\alpha_1\beta_1$ and $\alpha_2\beta_1$ participate in interactions between microvascular EC and polymeric collagen I (not shown).

Thus, the conclusion demonstrated and supported by the empirical data is that: (1) basal expression of $\alpha_1\beta_1$ and $\alpha_2\beta_1$ microvascular EC is not sufficient to promote cell spreading on collagen I gels; and (2) VEGF induction of $\alpha_1\beta_1$ and $\alpha_2\beta_1$ integrin expression correlates with EC spreading on collagen I gels; and (3) the spreading of VEGF prestimulated EC on collage I gels is abolished by a combination of $\alpha_1$-blocking MAb and $\alpha_2$-blocking MAb.

Experimental Series IV: Inhibition of VEGF-Driven Angiogenesis In-Vivo by MAbs which Specifically Block $\alpha_1$ and $\alpha_2$ To test directly the importance of $\alpha_1\beta_1$ and $\alpha_2\beta_1$ integrins for VEGF-driven angiogenesis in vivo, a mouse angiogenesis model was employed together with specific hamster monoclonal MAbs which specifically block only the murine $\alpha_1$ or $\alpha_2$ integrin subunits. The mouse angiogenesis model, which is a modified version of one described previously in the scientific literature [Passaniti et al., Lab. Invest. 67: 519–528 (1992)] involves subcutaneous injection of athymic nude mice with Matrigel containing human SK-MEL-2 tumor cells stably transfected for expression of murine $VEGF_{164}$. Untransfected SK-MEL-2 tumor cells are known to not provoke an angiogenic response; and therefore the angiogenic stimulus provided by the VEGF transfectants is entirely or predominantly attributable to VEGF. Furthermore, the hamster monoclonal MAbs specific for murine $\alpha_1$ and $\alpha_2$ integrin subunits do not recognize the respective human integrin subunits; and therefore those MAbs do not interact with the transfected SK-MEL-2 cells which provide the angiogenic stimulus.

Procedurally and experimentally, each animal received implants by subcutaneous injection, midway on the right and left back sides on day zero. Isotype-matched control Ab (300 μg) or a combination of $\alpha_1$ MAb and $\alpha_2$ MAb (150 μg each) were administered to the individual mouse by intraperitoneal injection on days 1, 3, and 5; and 5 animals were employed in each group under test. On day 6, all animals were sacrificed and dissected; the excised implants were photographed; and the excised tissues were fixed for histological analyses which included immunostaining for the EC marker CD31 (PECAM-1). Thus, a total of 20 implants were analyzed; 10 implants were derived from animals treated with control MAb and 10 implants were derived from animals treated with $\alpha_1$ MAb+$\alpha_2$ MAb. The empirical findings were highly consistent within each of the two groups, and typical examples are shown in FIGS. 8A–8D respectively.

FIG. 8 illustrates the inhibition of VEGF-driven angiogenesis in vivo by a combination of $\alpha_1$-blocking MAb and $\alpha_2$-blocking MAb.

Figure 8B:
Figure 8D:
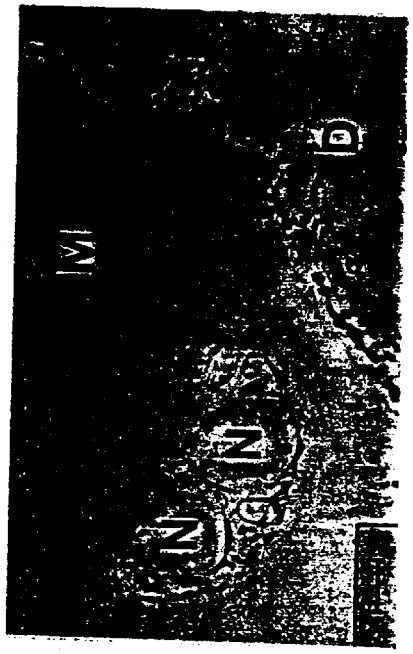
Figure 8A:
Figure 8C:
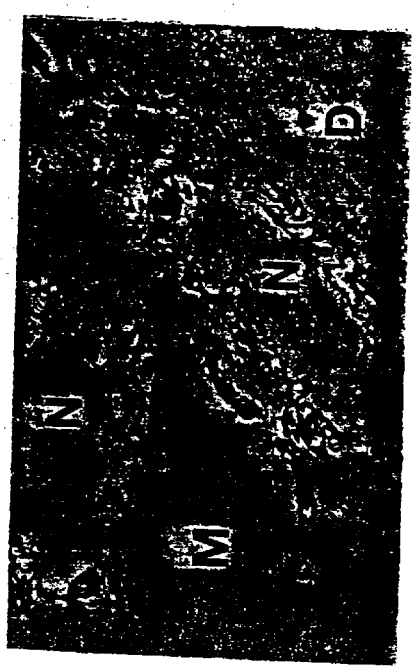

FIGS. 8A and 8B show the Matrigel implants (M) together with overlying skin. Note the reduced density of small blood vessels associated with implant from animal treated with $\alpha_1$ MAb+$\alpha_2$ MAb in FIG. 8B in comparison with FIG. 8A showing an animal treated with control Ab. In contrast, the larger pre-existing blood vessels appear unaffected. FIGS. 8C and 8D show the immunohistochemical staining for CD31 (blue color) which reveals that new blood vessels at the interface between the Matrigel implant (M) and host dermis (D), and in association with large nerves (N), were markedly reduced in cross-sectional area at sizes >90% in the $\alpha_1$ MAb+$\alpha_2$ MAb treated animals, in comparison with controls.

The evidence of FIGS. 8A–8D also clearly demonstrate that the overlying skin adjacent to the implants showed substantially reduced numbers of small blood vessels in the $\alpha_1$ MAb+$\alpha_2$ MAb treatment group in comparison with the control group (FIGS. 8A and 8B). Moreover, no detectable effects of MAb on the pre-existing blood vessels were observed. Consistent with these observations, the immunohistochemical staining for CD31 demonstrated that the average cross-sectional diameter of new blood vessels lying adjacent to the angiogenic stimulus was significantly ($p<0.001$) reduced in size to 8.4±1.5 μm in the $\alpha_1$ MAb+$\alpha_2$ MAb treatment group, in comparison with average diameter sizes of 31.6±4.3 μm in the control MAb group (FIGS. 8C and 8D). This significant reduction in average blood vessel diameter size translated into a >90% decrease in average cross-sectional area. Thus, the empirical results of these experiments are probative evidence that a combination of $\alpha_1$-blocking MAbs and $\alpha_2$-blocking MAbs potently inhibits VEGF-driven tumor angiogenesis in vivo without detectable adverse effects on the pre-existing vasculature.

SUMMARY OF EXPERIMENTAL DATA

The experiment described herein and the empirical findings reported here indicate that VEGF potently induces expression of specific $\alpha_1$ and $\alpha_2$ integrin subunits by microvascular EC. To summarize, the data show that:

(a) VEGF induces a 5- to 7-fold increase in dermal microvascular EC expression of $\alpha_1\beta_1$ and $\alpha_2\beta_1$ integrin heterodimers;
(b) on these microvascular EC, $\alpha_1\beta_1$ and $\alpha_2\beta_1$ both serve as receptors for collagen I and $\alpha_1\beta_1$ serves additionally as a receptor for collagen IV, collagen V, and laminin-1;
(c) VEGF induction of $\alpha_1\beta_1$ and $\alpha_2\beta_1$ promoted EC spreading on collagen I gels in vitro; and
(d) $\alpha_1$-blocking and $\alpha_2$-blocking monoclonal antibodies, in combination, markedly inhibit VEGF-driven tumor angiogenesis in vivo. Thus, the data indicate and reveal not only that VEGF induces $\alpha_1\beta_1$ and $\alpha_2\beta_1$ integrin heterodimers and collagen receptor expression by EC but also that $\alpha_1\beta_1$ and $\alpha_2\beta_1$ integrin receptor function is critical for VEGF-driven tumor angiogenesis.

The present invention is not to be limited in scope nor restricted in form except by the claims appended hereto.

---

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 147 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Xaa Asn His His Glu Val Val Lys Phe Met Asp Val Tyr Xaa
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Trp Ile Thr Met Gln Ile Met Arg Ile Lys Pro His
                100                 105                 110

Xaa Gly Xaa His Ile Gly Glu Met Ser Phe Leu Gln His Asn Lys Cys
            115                 120                 125

Glu Cys Arg Pro Pro Lys Asp Arg Ala Arg Gly Glu Lys Cys Asp Lys
        130                 135                 140

Pro Arg Arg
145
```

(2) INFORMATION FOR SEQ ID NO: 2:

(i) SEQUENCE CHARACTERISTICS:
      (A) LENGTH: 191 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Xaa Asn His His Glu Val Val Lys Phe Met Asp Val Tyr Xaa
            35                  40                  45

Arg Ser Tyr Cys His Pro Ile Glu Thr Leu Val Asp Ile Phe Gln Glu
50                      55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Trp Ile Thr Met Gln Ile Met Arg Ile Lys Pro His
                100                 105                 110

Xaa Gly Xaa His Ile Gly Glu Met Ser Phe Leu Gln His Asn Lys Cys
            115                 120                 125

Glu Cys Arg Pro Pro Lys Asp Arg Ala Arg Gly Glu Lys Pro Cys Gly
130                 135                 140

Pro Cys Ser Glu Arg Arg Lys His Leu Phe Val Xaa Asp Pro Xaa Thr
145                 150                 155                 160

Cys Lys Cys Ser Cys Lys Asn Thr Asp Ser Arg Cys Lys Ala Arg Xaa
                165                 170                 175

Leu Glu Lys Asn Glu Arg Thr Cys Arg Cys Asp Lys Pro Arg Arg
            180                 185                 190

(2) INFORMATION FOR SEQ ID NO: 3:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Xaa Asn His His Glu Val Val Lys Phe Met Asp Val Tyr Xaa
            35                  40                  45

Arg Ser Tyr Cys His Pro Ile Glu Thr Leu Val Asp Ile Phe Gln Glu
50                      55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Trp Ile Thr Met Gln Ile Met Arg Ile Lys Pro His
                100                 105                 110

Xaa Gly Xaa His Ile Gly Glu Met Ser Phe Leu Gln His Asn Lys Cys
            115                 120                 125

Glu Cys Arg Pro Lys Lys Asp Arg Ala Arg Gly Glu Lys Lys Ser Val
130                 135                 140

```
Arg Gly Lys Gly Gly Arg Gln Lys Arg Lys Lys Ser Arg Tyr
145                 150                 155                 160

Lys Ser Trp Ser Val Pro Cys Gly Pro Cys Ser Glu Arg Arg Lys His
            165                 170                 175

Leu Phe Val Xaa Asp Pro Xaa Thr Cys Lys Cys Ser Cys Lys Asn Thr
            180                 185                 190

Asp Ser Arg Cys Lys Ala Arg Xaa Leu Glu Lys Asn Glu Arg Thr Cys
            195                 200                 205

Arg Cys Asp Lys Pro Arg Arg
210                 215
```

(2) INFORMATION FOR SEQ ID NO: 4:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Xaa Asn His His Glu Val Val Lys Phe Met Asp Val Tyr Xaa
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Trp Ile Thr Met Gln Ile Met Arg Ile Lys Pro His
                100                 105                 110

Xaa Gly Xaa His Ile Gly Glu Met Ser Phe Leu Gln His Asn Lys Cys
            115                 120                 125

Glu Cys Arg Pro Lys Lys Asp Arg Ala Arg Gly Glu Lys Lys Ser Val
130                 135                 140

Arg Gly Lys Gly Gly Arg Gln Lys Arg Lys Lys Ser Arg Tyr
145                 150                 155                 160

Lys Ser Trp Ser Val Tyr Val Gly Ala Arg Cys Cys Leu Met Pro Trp
            165                 170                 175

Ser Leu Pro Gly Pro His Pro Cys Gly Pro Cys Ser Glu Arg Arg Lys
            180                 185                 190

His Leu Phe Val Xaa Asp Pro Xaa Thr Cys Lys Cys Ser Cys Lys Asn
            195                 200                 205

Thr Asp Ser Arg Cys Lys Ala Arg Xaa Leu Glu Lys Asn Glu Arg Thr
            210                 215                 220

Cys Arg Cys Asp Lys Pro Arg Arg
225                 230
```

(2) INFORMATION FOR SEQ ID NO: 5:

(i) SEQUENCE CHARACTERISTICS:
        (A) LENGTH: 1183 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO: 5:

```
Met Val Pro Arg Arg Pro Ala Ser Leu Glu Val Thr Val Thr Val Ala
1               5                   10                  15

Cys Ile Trp Leu Leu Thr Val Ile Leu Gly Phe Cys Val Ser Phe Asn
            20                  25                  30

Val Asp Val Lys Asn Ser Met Thr Phe Ser Gly Pro Val Glu Asp Met
        35                  40                  45

Phe Gly Tyr Thr Val Gln Gln Tyr Glu Asn Glu Glu Gly Lys Trp Val
    50                  55                  60

Leu Ile Gly Ser Pro Leu Val Gly Gln Pro Lys Asn Arg Thr Gly Asp
65                  70                  75                  80

Val Tyr Lys Cys Pro Val Gly Arg Gly Glu Ser Leu Pro Cys Val Lys
                85                  90                  95

Leu Asp Leu Pro Val Asn Thr Ser Ile Pro Asn Val Thr Glu Val Lys
                100                 105                 110

Glu Asn Met Thr Phe Gly Ser Thr Leu Val Thr Asn Pro Asn Gly Gly
            115                 120                 125

Phe Leu Ala Cys Gly Pro Leu Tyr Ala Tyr Arg Cys Gly His Leu His
    130                 135                 140

Tyr Thr Thr Gly Ile Cys Ser Asp Val Ser Pro Thr Phe Gln Val Val
145                 150                 155                 160

Asn Ser Ile Ala Pro Val Gln Glu Cys Ser Thr Xaa Leu Asp Ile Val
                165                 170                 175

Ile Val Leu Asp Gly Ser Asn Ser Ile Tyr Pro Met Asp Ser Val Thr
            180                 185                 190

Ala Leu Asn Asp Leu Leu Lys Arg Met Asp Ile Gly Pro Lys Xaa Thr
            195                 200                 205

Xaa Val Gly Ile Val Xaa Tyr Gly Glu Asn Val Thr His Glu Phe Asn
    210                 215                 220

Leu Asn Lys Tyr Ser Ser Thr Glu Glu Val Leu Val Ala Ala Lys Lys
225                 230                 235                 240

Ile Val Xaa Arg Gly Gly Arg Xaa Thr Met Thr Ala Leu Gly Thr Asp
                245                 250                 255

Thr Ala Arg Lys Glu Ala Phe Thr Glu Ala Arg Gly Ala Arg Arg Gly
            260                 265                 270

Val Lys Lys Val Met Val Ile Val Thr Asp Gly Glu His Asp Xaa Asn
            275                 280                 285

His Arg Leu Lys Lys Val Ile Gly Asp Cys Glu Asp Glu Asn Ile Xaa
    290                 295                 300

Arg Phe Ser Ile Ala Ile Leu Gly Ser Tyr Asn Arg Gly Asn Leu Ser
305                 310                 315                 320

Thr Glu Lys Phe Val Glu Glu Ile Lys Ser Ile Ala Ser Glu Pro Thr
                325                 330                 335

Glu Lys Ser Phe Phe Asn Val Ser Asp Glu Leu Ala Leu Val Thr Ile
            340                 345                 350

Val Lys Thr Leu Gly Glu Arg Ile Phe Ala Leu Glu Ala Thr Ala Asp
        355                 360                 365

Xaa Ser Ala Ala Ser Phe Glu Met Glu Met Ser Gln Thr Gly Phe Ser
370                 375                 380
```

-continued

```
Ala His Tyr Ser Gln Asp Met Val Trp Leu Gly Ala Val Gly Ala Tyr
385                 390                 395                 400

Asp Trp Asn Gly Thr Val Val Asn Gln Lys Ala Ser Gln Ile Ile Ile
            405                 410                 415

Pro Arg Asn Thr Thr Phe Asn Val Glu Ser Thr Lys Lys Asn Glu Pro
            420                 425                 430

Leu Ala Ser Tyr Leu Gly Tyr Thr Val Asn Ser Ala Thr Ala Ser Ser
            435                 440                 445

Gly Asp Val Leu Tyr Ile Ala Gly Gln Pro Arg Tyr Asn His Thr Gly
    450                 455                 460

Gln Val Ile Ile Tyr Arg Met Glu Glu Gly Asn Ile Lys Ile Leu Gln
465                 470                 475                 480

Thr Leu Ser Gly Glu Xaa Ile Gly Ser Tyr Phe Gly Ser Ile Leu Thr
                485                 490                 495

Thr Thr Asp Ile Asp Lys Asp Ser Asn Thr Asn Ile Leu Leu Val Gly
                500                 505                 510

Ala Pro Met Tyr Met Gly Thr Glu Lys Glu Gly Gly Lys Val Tyr
                515                 520                 525

Val Tyr Ala Leu Asn Gln Thr Arg Phe Glu Tyr Gln Met Ser Leu Ala
530                 535                 540

Pro Met Glu Pro Ile Lys Gln Thr Cys Cys Ser Ser Arg Gln His Asn
545                 550                 555                 560

Ser Cys Thr Thr Glu Asn Lys Asn Glu Pro Cys Gly Ala Arg Phe Gly
                565                 570                 575

Thr Ala Ile Ala Ala Val Lys Asp Leu Asn Leu Asp Gly Phe Asn Asp
                580                 585                 590

Ile Val Ile Gly Ala Pro Leu Glu Asp Asp His Gly Gly Ala Val Tyr
                595                 600                 605

Ile Tyr His Gly Ser Gly Lys Thr Ile Arg Lys Glu Tyr Ala Xaa Arg
                610                 615                 620

Ile Pro Ser Gly Gly Asp Gly Lys Thr Leu Lys Phe Phe Gly Gln Ser
625                 630                 635                 640

Ile His Gly Glu Met Asp Leu Asn Gly Asp Gly Leu Thr Asp Val Thr
                645                 650                 655

Ile Cys Gly Leu Gly Gly Ala Ala Leu Phe Trp Ser Arg Asp Val Ala
                660                 665                 670

Val Val Lys Val Thr Met Asn Phe Glu Pro Asn Lys Val Asn Ile Gln
                675                 680                 685

Lys Lys Asn Cys His Met Glu Gly Lys Glu Thr Val Cys Ile Asn Ala
690                 695                 700

Thr Val Cys Phe Glu Val Lys Leu Lys Ser Lys Glu Asp Thr Ile Tyr
705                 710                 715                 720

Glu Ala Asp Leu Gln Tyr Arg Val Thr Leu Asp Ser Leu Arg Gln Ile
                725                 730                 735

Ser Arg Ser Phe Phe Ser Gly Thr Gln Glu Arg Lys Val Gln Arg Asn
                740                 745                 750

Ile Thr Val Arg Lys Ser Glu Cys Thr Lys His Ser Phe Tyr Met Leu
                755                 760                 765

Asp Lys His Asp Phe Gln Asp Ser Val Arg Ile Thr Leu Asp Phe Asn
                770                 775                 780

Leu Thr Asp Pro Glu Asn Gly Pro Val Leu Asp Asp Ser Leu Pro Asn
785                 790                 795                 800
```

```
Ser Val His Glu Tyr Ile Pro Phe Ala Lys Asp Cys Gly Asn Lys Glu
            805                 810                 815

Lys Cys Ile Ser Asp Leu Ser Leu His Val Ala Thr Thr Glu Lys Asp
            820                 825                 830

Leu Leu Ile Val Arg Ser Gln Asn Asp Lys Phe Asn Val Ser Leu Thr
            835                 840                 845

Val Lys Asn Thr Lys Asp Ser Ala Tyr Asn Thr Arg Thr Ile Val His
850                 855                 860

Tyr Ser Pro Asn Leu Val Phe Ser Gly Ile Glu Ala Ile Gln Lys Asp
865                 870                 875                 880

Ser Cys Glu Ser Asn His Asn Ile Thr Cys Lys Val Gly Tyr Pro Phe
            885                 890                 895

Leu Arg Arg Gly Glu Met Val Thr Phe Lys Ile Leu Phe Gln Phe Asn
            900                 905                 910

Thr Ser Tyr Leu Met Glu Asn Val Thr Ile Tyr Leu Ser Ala Thr Ser
            915                 920                 925

Asp Ser Glu Glu Pro Pro Glu Thr Leu Ser Asp Asn Val Val Asn Ile
930                 935                 940

Ser Ile Pro Val Lys Tyr Glu Val Gly Leu Gln Phe Tyr Ser Ser Ala
945                 950                 955                 960

Ser Glu Tyr His Ile Ser Ile Ala Ala Asn Glu Thr Val Pro Glu Val
            965                 970                 975

Ile Asn Ser Thr Glu Asp Ile Gly Asn Glu Ile Asn Ile Phe Tyr Leu
            980                 985                 990

Ile Arg Lys Ser Gly Ser Phe Pro Met Pro Glu Leu Lys Leu Ser Ile
            995                 1000                1005

Ser Phe Pro Asn Met Thr Ser Asn Gly Tyr Pro Val Leu Val Pro Thr
            1010                1015                1020

Gly Leu Ser Ser Glu Asn Ala Asn Cys Arg Pro His Ile Phe Glu
1025                1030                1035                1040

Asp Pro Phe Ser Ile Asn Ser Gly Lys Lys Met Thr Thr Ser Thr Asp
            1045                1050                1055

His Leu Lys Arg Gly Thr Ile Leu Asp Cys Asn Thr Cys Lys Phe Ala
            1060                1065                1070

Thr Ile Thr Cys Asn Leu Thr Ser Ser Asp Ile Ser Xaa Val Asn Val
            1075                1080                1085

Ser Leu Ile Leu Trp Lys Pro Thr Phe Ile Lys Ser Tyr Phe Ser Ser
            1090                1095                1100

Leu Asn Leu Thr Ile Arg Gly Glu Leu Arg Ser Glu Asn Ala Ser Leu
1105                1110                1115                1120

Val Leu Ser Ser Asn Glu Lys Arg Glu Leu Ala Ile Gln Ile Ser
            1125                1130                1135

Lys Asp Gly Leu Pro Gly Arg Val Pro Leu Trp Val Ile Leu Leu Ser
            1140                1145                1150

Ala Phe Ala Gly Leu Leu Leu Leu Met Leu Leu Ile Leu Ala Leu Trp
            1155                1160                1165

Lys Ile Gly Phe Phe Lys Arg Pro Leu Lys Lys Met Glu Lys
            1170                1175                1180
```

(2) INFORMATION FOR SEQ ID NO: 6:

(i) SEQUENCE CHARACTERISTICS:
        (A) LENGTH: 1183 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO: 6:

```
Met Gly Pro Glu Arg Thr Gly Ala Ala Pro Leu Pro Leu Leu Val
1               5                   10                  15

Leu Ala Leu Ser Gln Gly Ile Leu Asn Cys Cys Leu Ala Tyr Asn Val
                20                  25                  30

Gly Leu Pro Glu Ala Lys Ile Phe Ser Gly Pro Ser Ser Glu Gln Phe
            35                  40                  45

Gly Tyr Ala Val Gln Gln Phe Ile Asn Pro Lys Gly Asn Trp Leu Leu
        50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
                85                  90                  95

Leu Gln Thr Ser Thr Ser Ile Pro Asn Val Thr Glu Met Lys Thr Asn
                100                 105                 110

Met Ser Leu Gly Leu Ile Leu Thr Arg Asn Met Gly Thr Gly Gly Phe
            115                 120                 125

Leu Thr Cys Gly Pro Leu Trp Ala Gln Gln Cys Gly Asn Gln Tyr Tyr
    130                 135                 140

Thr Thr Gly Val Cys Ser Asp Ile Ser Pro Asp Phe Xaa Lys Ser Ala
145                 150                 155                 160

Ser Phe Ser Pro Ala Thr Xaa Pro Cys Pro Ser Leu Ile Asp Val Val
                165                 170                 175

Val Val Cys Asp Glu Ser Asn Ser Ile Tyr Pro Trp Asp Ala Val Lys
            180                 185                 190

Asn Phe Leu Glu Lys Phe Val Gln Gly Leu Asp Ile Gly Pro Thr Lys
        195                 200                 205

Thr Gln Val Gly Leu Ile Gln Tyr Ala Asn Asn Pro Arg Val Val Phe
    210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
                245                 250                 255

Gln Tyr Ala Arg Lys Tyr Ala Tyr Ser Ala Ala Ser Gly Gly Arg Arg
            260                 265                 270

Ser Ala Thr Lys Val Met Val Val Val Thr Asp Gly Glu Ser His Asp
        275                 280                 285

Gly Ser Met Leu Lys Ala Val Ile Asp Gln Cys Asn His Asp Asn Ile
    290                 295                 300

Leu Arg Phe Gly Ile Ala Val Leu Gly Tyr Leu Asn Arg Asn Ala Leu
305                 310                 315                 320

Asp Thr Lys Met Asn Leu Ile Lys Glu Ile Lys Ala Ile Ala Ser Ile
                325                 330                 335

Pro Thr Glu Arg Tyr Phe Phe Asn Val Ser Asp Glu Ala Ala Leu Leu
            340                 345                 350

Glu Lys Ala Gly Thr Leu Gly Glu Gln Ile Phe Ser Ile Glu Gly Thr
        355                 360                 365

Val Xaa Gly Gly Asp Asn Phe Xaa Met Glu Met Ser Gln Val Gly Phe
370                 375                 380
```

-continued

```
Ser Ala Asp Tyr Ser Ser Gln Asn Asp Ile Leu Met Leu Gly Ala Val
385                 390                 395                 400

Gly Ala Phe Gly Trp Ser Gly Thr Ile Val Gln Lys Thr Ser His Gly
            405                 410                 415

His Leu Ile Phe Pro Lys Gln Ala Phe Asp Gln Ile Gln Asp Arg Asn
            420                 425                 430

His Ser Ser Tyr Leu Gly Tyr Ser Val Ala Ala Ile Ser Thr Gly Glu
            435                 440                 445

Ser Thr His Phe Val Ala Gly Ala Pro Arg Ala Asn Val Thr Gly Gln
        450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
            485                 490                 495

Ser Val Asp Val Asp Lys Asp Thr Ile Thr Asp Val Leu Leu Val Gly
            500                 505                 510

Ala Pro Met Tyr Met Ser Asp Leu Lys Lys Glu Glu Gly Arg Val Tyr
        515                 520                 525

Leu Phe Thr Ile Lys Lys Gly Ile Leu Gly Gln His Gln Phe Leu Glu
        530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
            565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
        610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
            645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
        690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
            725                 730                 735

Cys Pro Glu His Ile Ile Tyr Ile Gln Glu Pro Ser Asp Val Val Asn
            740                 745                 750

Ser Leu Asp Asp Leu Arg Val Asp Ile Ser Leu Glu Asn Pro Gly Thr
        755                 760                 765

Ser Pro Ala Leu Glu Ala Tyr Ser Glu Thr Ala Lys Val Phe Ser Ile
        770                 775                 780

Pro Phe His Lys Asp Cys Gly Glu Asp Gly Lys Cys Ile Ser Asp Leu
785                 790                 795                 800
```

-continued

```
Val Leu Gln Asp Val Arg Ile Pro Ala Ala Gln Glu Gln Pro Phe Ile
            805                 810                 815

Val Ser Asn Gln Asn Lys Arg Leu Thr Phe Ser Val Thr Leu Lys Asn
        820                 825                 830

Lys Arg Glu Ser Ala Tyr Asn Thr Gly Ile Val Val Asp Phe Ser Glu
    835                 840                 845

Asn Leu Phe Phe Ala Ser Phe Ser Leu Pro Val Asp Gly Thr Glu Val
850                 855                 860

Thr Cys Gln Val Ala Ala Ser Gln Lys Ser Val Ala Cys Asp Val Gly
865                 870                 875                 880

Tyr Pro Ala Leu Lys Arg Glu Gln Gln Val Thr Phe Thr Ile Asn Phe
                885                 890                 895

Asp Phe Asn Leu Gln Asn Leu Gln Asn Gln Ala Ser Leu Ser Phe Gln
            900                 905                 910

Ala Leu Ser Glu Ser Gln Glu Glu Asn Lys Ala Asp Asn Leu Val Asn
        915                 920                 925

Leu Lys Ile Phe Leu Leu Tyr Asp Ala Glu Ile His Leu Thr Arg Ser
    930                 935                 940

Thr Asn Ile Asn Phe Tyr Glu Ile Ser Ser Asp Gly Asn Val Pro Ser
945                 950                 955                 960

Ile Val His Ser Phe Glu Asp Val Gly Pro Lys Phe Ile Phe Ser Leu
                965                 970                 975

Lys Val Thr Thr Gly Ser Val Pro Val Ser Met Ala Thr Val Ile Ile
            980                 985                 990

His Ile Pro Gln Tyr Thr Lys Glu Lys Asn Pro Leu Met Tyr Leu Thr
        995                 1000                1005

Gly Val Gln Thr Asp Lys Ala Gly Asp Ile Cys Cys Asn Ala Asp Ile
    1010                1015                1020

Asn Pro Leu Lys Ile Gly Gln Thr Ser Ser Val Ser Phe Lys Ser
1025                1030                1035                1040

Glu Asn Phe Arg His Thr Lys Glu Leu Asn Cys Arg Thr Ala Ser Cys
                1045                1050                1055

Ser Asn Val Thr Cys Trp Leu Asp Val His Met Lys Gly Glu Tyr
            1060                1065                1070

Phe Val Asn Val Thr Thr Arg Ile Trp Asn Gly Thr Phe Ala Ser Ser
        1075                1080                1085

Thr Phe Gln Thr Val Gln Leu Thr Ala Ala Glu Ile Asn Thr Tyr
    1090                1095                1100

Asn Pro Glu Ile Tyr Val Ile Glu Asp Asn Thr Val Thr Ile Pro Leu
1105                1110                1115                1120

Met Ile Met Lys Pro Asp Glu Lys Ala Glu Val Pro Thr Gly Val Ile
                1125                1130                1135

Ile Gly Ser Ile Ile Ala Gly Ile Leu Leu Leu Leu Ala Leu Val Ala
            1140                1145                1150

Ile Leu Trp Lys Leu Gly Phe Phe Lys Arg Lys Tyr Glu Lys Met Thr
        1155                1160                1165

Lys Lys Asn Pro Asp Glu Ile Asp Glu Thr Thr Glu Leu Ser Ser
    1170                1175                1180
```

What we claim is:

1. A method for inhibiting tumor angiogenesis mediated by vascular endothelial growth factor (VEGF) and integrin cell surface receptors expressed in the vasculature of a living subject wherein said subject has a tumor, said method comprising the steps of:

allowing mobile VEGF secreted by a tumor mass present within the body of a living subject to become bound in-vivo to the surface of endothelial cells in a tumor-associated blood vessel, permitting said bound VEGF to induce the expression of specific integrin heterodimers on the endothelial cell surface of the tumor-associated blood vessel in-vivo, said specifically induced and expressed integrin heterodimers being selected from the group consisting of integrins composed of $\alpha_1$ and $\alpha_2$ integrin subunits; and then administering to the living subject at least one function-blocking antagonistic antibody preparation effective against said specifically induced and expressed specified integrin heterodimers on the endothelial cell surface of the tumor-associated blood vessel such that tumor angiogenesis is inhibited in-vivo, said function-blocking antagonistic preparation comprising at least one antibody specific for an integrin subunit selected from the group consisting of the $\alpha_1$ and $\alpha_2$ integrin subunits.

2. A method for inhibiting tumor angiogenesis mediated by vascular endothelial growth factor (VEGF) and integrin cell surface receptors expressed in the vasculature of a living subject wherein said subject has a tumor, said method comprising the steps of:

allowing mobile VEGF secreted by a tumor mass present within the body of a living subject to become bound in-vivo to the surface of endothelial cells in a tumor-included blood vessel;

permitting said bound VEGF to induce the expression of specific integrin heterodimers on the endothelial cell surface of the tumor-included blood vessel in-vivo, said specifically induced and expressed integrin heterodimers being selected from the group consisting of integrins composed of $\alpha_1$ and $\alpha_2$ integrin subunits; and then administering to the living subject at least one function-blocking antagonistic antibody preparation effective against said specifically induced and expressed specified integrin heterodimers on the endothelial cell surface of the tumor-included blood vessel such that tumor angiogenesis is inhibited in-vivo, said function-blocking antagonistic preparation comprising at least one antibody specific for an integrin subunit selected from the group consisting of the $\alpha_1$ and $\alpha_2$ integrin subunits.

3. A method for inhibiting tumor angiogenesis as recited in claim 1 or 2 wherein said function-blocking antagonistic antibody preparation is a monoclonal antibody.

4. The method for inhibiting tumor angiogenesis as recited in claim 1 or 2 wherein said function-blocking antagonistic antibody preparation is a polyclonal antibody preparation.

5. The method for inhibiting tumor angiogenesis as recited in claim 1 or 2 wherein said function-blocking antagonistic antibody preparation includes at least one entity selected from the group consisting of Fab, F(ab)$_2$, humanized, and genetically engineered antibody fragments.

6. A method for inhibiting tumor angiogenesis mediated by vascular endothelial growth factor (VEGF) and integrin cell surface receptors expressed in the vasculature of a living subject wherein said subject has a tumor, said method comprising the steps of:

allowing mobile VEGF secreted by a tumor mass present within the body of a living subject to become bound in-vivo to the surface of endothelial cells in a tumor-associated blood vessel, permitting said bound VEGF to induce the expression of specified integrin heterodimers on the endothelial cell surface of the tumor-associated blood vessel in-vivo, said induced and expressed integrin heterodimers being selected from the group consisting of integrins composed of $\alpha_1$ and $\alpha_2$ integrin subunits; and then administering at least one function-blocking antagonistic antibody preparation effective against said induced and expressed specified integrin heterodimers on the endothelial cell surface to the living subject such that tumor angiogenesis is inhibited in-vivo, said function-blocking antagonistic preparation comprising a mixture of antibodies specific for the $\alpha_1$ and $\alpha_2$ integrin subunits.

7. A method for inhibiting tumor angiogenesis mediated by vascular endothelial growth factor (VEGF) and integrin cell surface receptors expressed in the vasculature of a living subject wherein said subject has a tumor, said method comprising the steps of:

allowing mobile VEGF secreted by a tumor mass present within the body of a living subject to become bound in-vivo to the surface of endothelial cells in a tumor-included blood vessel;

permitting said bound VEGF to induce the expression of specified integrin heterodimers on the endothelial cell surface of the tumor-included blood vessel in-vivo, said induced and expressed integrin heterodimers being selected from the group consisting of integrins composed of $\alpha_1$ and $\alpha_2$ integrin subunits; and then administering at least one function-blocking antagonistic antibody preparation effective against said induced and expressed specified integrin heterodimers on the endothelial cell surface to the living subject such that tumor angiogenesis is inhibited in-vivo, said function-blocking antagonistic preparation comprising a mixture of antibodies specific for the $\alpha_1$ and $\alpha_2$ integrin subunits.

* * * * *